(12) United States Patent
Nirogi et al.

(10) Patent No.: US 8,598,204 B2
(45) Date of Patent: Dec. 3, 2013

(54) 1,2-DIHYDRO-2-OXOQUINOLINE COMPOUNDS AS 5-HT$_4$ RECEPTOR LIGANDS

(75) Inventors: Ramakrishna Nirogi, Hyderabad (IN); Abdul Rasheed Mohammed, Hyderabad (IN); Ishtiyaque Ahmad, Hyderabad (IN); Pradeep Jayarajan, Hyderabad (IN); Nagaraj Vishwottam Kandikere, Hyderabad (IN); Anil Karbhari Shinde, Hyderabad (IN); Rama Sastri Kambhampati, Hyderabad (IN); Gopinadh Bhyrapuneni, Hyderabad (IN); Jyothsna Ravula, Hyderabad (IN); Sriramachandra Murthy Patnala, Hyderabad (IN); Venkateswarlu Jasti, Hyderabad (IN)

(73) Assignee: Suven Life Sciences Limited, Hyderabad (IN)

( * ) Notice: Subject to any disclaimer, the term of this patent is extended or adjusted under 35 U.S.C. 154(b) by 91 days.

(21) Appl. No.: 13/393,539

(22) PCT Filed: Dec. 29, 2009

(86) PCT No.: PCT/IN2009/000745
§ 371 (c)(1),
(2), (4) Date: Apr. 13, 2012

(87) PCT Pub. No.: WO2011/030349
PCT Pub. Date: Mar. 17, 2011

(65) Prior Publication Data
US 2012/0277216 A1   Nov. 1, 2012

(30) Foreign Application Priority Data

Sep. 14, 2009   (IN) ................. 2224/CHE/2009

(51) Int. Cl.
*A61K 31/04*   (2006.01)
*C07D 215/38*   (2006.01)

(52) U.S. Cl.
USPC .......... 514/312; 514/291; 514/292; 546/154; 546/156; 546/97; 546/81

(58) Field of Classification Search
USPC .......... 514/312, 291, 292; 546/154, 156, 97, 546/81
See application file for complete search history.

(56) References Cited

U.S. PATENT DOCUMENTS

| | | | |
|---|---|---|---|
| 5,726,187 | A | 3/1998 | Gaster et al. |
| 7,405,235 | B2 * | 7/2008 | Levy et al. ............ 514/394 |
| 7,419,989 | B2 | 9/2008 | Fatheree et al. |
| 7,534,889 | B2 | 5/2009 | Choi et al. |
| 2006/0100236 | A1 | 5/2006 | Choi et al. |
| 2006/0194842 | A1 | 8/2006 | Uchida et al. |
| 2008/0207690 | A1 | 8/2008 | Noguchi et al. |
| 2008/0269211 | A1 | 10/2008 | Ishibashi et al. |
| 2011/0021557 | A1 * | 1/2011 | Dhanoa ............ 514/301 |

OTHER PUBLICATIONS

A. Dumuis et al; A 5-HT receptor in the central nervous system, positively coupled with adenylate cyclase, is antagonized by ICS 205 930; European Journal of Pharmacology, 146 (19988) 187-188, 1988.
A. Dumuis et al; A Nonclassical 5-Hydroxytryptamine Receptor Positively Coupled with Adenylate Cyclase in the Central Nervous System; The American Society for Pharmacology and Experimental Therapeutics, Molecular Pharmacology, 34: 880-887, 1988.
P. B. Bradley et al; Proposal for the Classification and Nomenclature of Functional Receptors for 5-Hydroxytryptamine; Neuropharmacology vol. 25, No. 6, pp. 563-576, 1986.
P.P.A. Humphrey et al; A Proposed New Nomenclature for 5-HT Receptors; TiPS—Jun. 1993, vol. 14; Elsevier Science Publishers Ltd.; pp. 233-236.
Anthony P.D.W. Ford et al; The 5-HT4 Receptor; Medicinal Research Reviews, vol. 13, No. 6, 633-662 (1993); John Wiley & Sons, Inc.
M. Corsi et al; Pharmacological Analysis of 5-Hydroxytryptamine Effects on Electrically Stimulated Human Isolated Urinary Bladder; Br. J. Pharmacol (1991) 104, pp. 719-725.
Manoj V. Waikar et al; Evidence for an Inhibitory 5-HT4 Receptor in Urinary Bladder of Rhesus and Cynomolgus Monkeys; Br. J. Pharmacol. 1994, 111, pp. 213-218.
Gary W. Gullikson et al; Gastrointestinal Motility Response to the S and R Enantiomers of Zacopride, a 5-HT4 Agonist and 5-HT3 Antagonist; Drug Development Research 26;405-417 (1992).
Alberto J. Kaumann et al; A 5-HT4-like Receptor in Human Right Atrium; Naunyn-Schmiedeberg's Arch Pharmacol (1991) 344; 150-159.
European Patent Office; International Preliminary Report on Patentability; PCT/IN2009/000745, corresponding to the instant US application; Aug. 11, 2011.

* cited by examiner

*Primary Examiner* — D M Seaman
(74) *Attorney, Agent, or Firm* — Iphorgan Ltd.

(57) ABSTRACT

The present invention relates to novel 1,2-dihydro-2-oxoquinoline compounds of the formula (I), and their derivatives, prodrugs, tautomers, stereoisomers, polymorphs, solvates, hydrates, metabolites, N-oxides, pharmaceutically acceptable salts and compositions containing them.

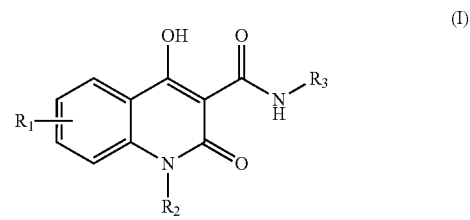

(I)

The present invention also relates to a process for the preparation of above said novel compounds, and their derivatives, prodrugs, tautomers, stereoisomers, polymorphs, solvates, hydrates, metabolites, N-oxides, pharmaceutically acceptable salts and compositions containing them.
The compounds of the present invention are useful in the treatment/prevention of various disorders that are mediated by 5-HT4 receptor activity.

6 Claims, No Drawings

1,2-DIHYDRO-2-OXOQUINOLINE COMPOUNDS AS 5-$HT_4$ RECEPTOR LIGANDS

CROSS-REFERENCE TO RELATED APPLICATIONS

This application claims the benefit of International Application No. PCT/IN2009/000745, filed on Dec. 29, 2009, which in turn claims priority to Indian Patent Application No. 2224/CHE/2009, filed Sep. 14, 2009, the contents of which are both hereby incorporated by reference.

FIELD OF INVENTION

The present invention relates to novel 1,2-dihydro-2-oxoquinoline compounds of the formula (I), and their derivatives, prodrugs, tautomers, stereoisomers, polymorphs, solvates, hydrates, metabolites, N-oxides, pharmaceutically acceptable salts and compositions containing them.

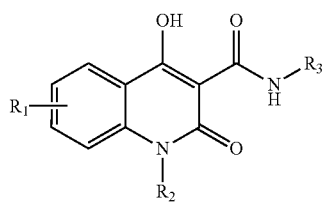

(I)

The present invention also relates to a process for the preparation of above said novel compounds, and their derivatives, prodrugs, tautomers, stereoisomers, polymorphs, solvates, hydrates, metabolites, N-oxides, pharmaceutically acceptable salts and compositions containing them.

The compounds of the present invention are useful in the treatment/prevention of various disorders that are mediated by 5-$HT_4$ receptor activity.

BACKGROUND OF THE INVENTION

The serotonin (5-hydroxytryptamine, 5-HT) receptors are a group of G protein-coupled receptors (GPCRs) and ligand-gated ion channels (LGICs) found in the central and peripheral nervous systems. The 5-HT receptor family is presently delineated into seven major sub classifications, 5-$HT_1$ family (e.g. 5-$HT_{1A}$), the 5-$HT_2$ family (e.g. 5-$HT_{2A}$ & 5-$HT_{2C}$), 5-$HT_3$, 5-$HT_4$, 5-$HT_5$, 5-$HT_6$ and 5-$HT_7$ and the interaction of serotonin with these different receptors is linked to a wide variety of physiological functions. There has been, therefore, substantial interest in developing therapeutic agents that target specific 5-HT receptor subtypes A novel 5-hydroxytryptamine (5-HT) receptor, positively coupled with adenylate cyclase was identified in mouse embryo colliculi neurones by Dumuis and co-workers in 1988 (Dumuis et al., 1988a, b). The receptor was tentatively named 5-$HT_4$ due to its inability to fit into the Bradley et al. (1986) classification. Since then, the 5-$HT_4$ receptor has been officially recognized (Humphrey et al., 1993) and identified in a variety of tissues across many species (for review see Ford & Clarke, 1993). In particular, characterization of 5-$HT_4$ receptors and identification of pharmaceutical agents that interact with them has been the focus of significant recent activity. (See, for example, the review by Langlois and Fischmeister, 5-$HT_4$ Receptor Ligands: Applications and New Prospects J. Med. Chem. 2003, 46, 319-344.)

5-$HT_4$ receptor modulators (e.g., agonists and antagonists) are found to be useful for the treatment of a variety of diseases such as gastroesophageal reflux disease, gastrointestinal disease, gastric motility disorder, non-ulcer dyspepsia, functional dyspepsia, irritable bowel syndrome, constipation, dyspepsia, esophagitis, gastroesophageral disease, nausea, central nervous system diseases, alzheimers disease, cognitive disorder, emesis, migraine, neurological disease, pain, and cardiovascular disorders such as cardiac failure and heart arrhythmia (Corsi. M et al., Pharmacological analysis of 5-hydroxytryptamine effects on electrically stimulated human isolated urinary bladder, Br. J. Pharmacol. 1991, 104 (3), 719-725; Waikar. M. V et al., Evidence for an inhibitory 5-$HT_4$ receptor in urinary bladder of rhesus and Cynomolgus monkeys, Br. J. Pharmacol. 1994, 111(1), 213-218; Anthony P. D. W. Ford et al., The 5-$HT_4$ Receptor, Med. Res. Rev. 1993, 13(6), 633-662; Gary W. Gullikson et al., Gastrointestinal motility responses to the S and R enantiomers of zacopride a 5-$HT_4$ agonist and 5-$HT_3$ antagonist, Drug Dev. Res. 1992, 26(4), 405-417; Kaumann. A. J et al., A 5-$HT_4$-like receptor in human right atrium, Naunyn-Schmiedeberg's Arch. Pharmacol. 1991, 344(2), 150-159).

USA patents/patent publications U.S. Pat. No. 5,726,187, U.S. Pat. No. 7,419,989, U.S. Pat. No. 7,534,889, US20060194842, US20080207690 and US20080269211 disclosed some 5-$HT_4$ receptor compounds. While some 5-$HT_4$ modulators have been disclosed, there continues to be a need for compounds that are useful for modulating 5-$HT_4$. Our quest for finding novel and potent ligands as 5-$HT_4$ receptor modulators had resulted in the discovery of 1,2-dihydro-2-oxoquinoline compounds of the formula (I) demonstrating very high 5-$HT_4$ receptor affinity. Therefore, it is an object of this invention to provide compounds, which are useful as therapeutic agents in the treatment/prevention of a variety of disorders or disorders affected by the 5-$HT_4$ receptor.

SUMMARY OF THE INVENTION

The present invention relates to novel 5-$HT_4$ receptor ligand compounds of the formula (I), and their derivatives, prodrugs, tautomers, stereoisomers, polymorphs, solvates, hydrates, metabolites, N-oxides, pharmaceutically acceptable salts and compositions containing them

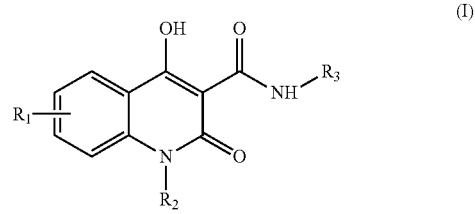

(I)

wherein $R_1$ represents hydrogen, hydroxy, halogen, haloalkyl, haloalkoxy, nitro, amide, amine, cyano, carboxylic, cycloalkyl, alkyl, alkenyl, alkynyl, alkoxy, aryl, aralkyl, heteroaryl, heteroaralkyl or heterocyclyl;

$R_2$ represents hydrogen, alkyl, cycloalkyl, aryl, aralkyl, heteroaryl, heteroaralkyl or heterocyclyl;

R3 represents

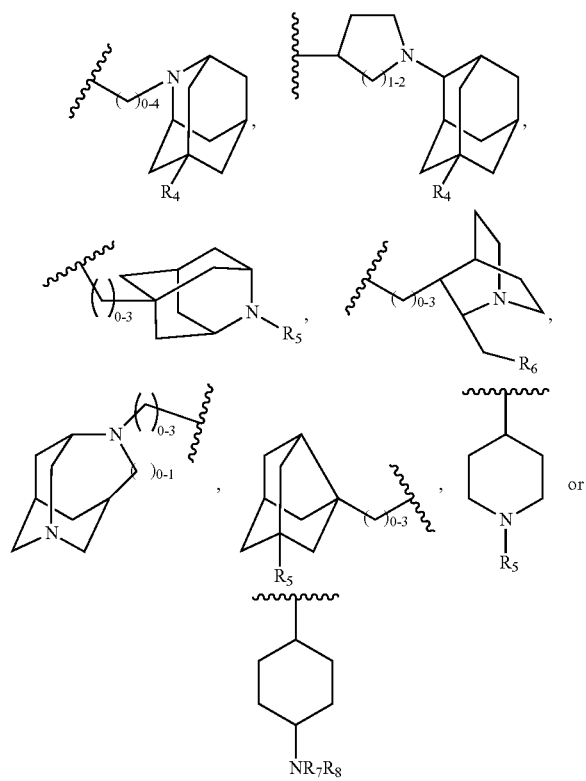

R4 represents hydrogen, hydroxy, amine; alkyl, alkoxy, aryl, aryloxy, cycloalkyl, cycloalkoxy, heteroaryl, heteroaralkyl or heterocyclyl;

R5 represents hydrogen, alkyl, cycloalkyl or heterocyclyl;

R6 represents heteroaryl;

R7 and R8 represent hydrogen, alkyl, cycloalkyl or heterocyclyl;

Optionally R7 and R8 along with 'N' atom may form 4 to 9 member rings, which includes one or more heteroatoms selected from C, O, N, S The present invention relates to use of a therapeutically effective amount of compound of formula (I), to manufacture a medicament in the treatment/prevention of various disorders that are related to 5-HT$_4$ receptors.

Specifically, the compounds of this invention are useful in the treatment of various disorders such as gastroesophageal reflux disease, gastrointestinal disease, gastric motility disorder, non-ulcer dyspepsia, functional dyspepsia, irritable bowel syndrome, constipation, dyspepsia, esophagitis, gastroesophageal disease, nausea, central nervous system disease, Alzheimer's disease, cognitive disorder, emesis, migraine, neurological disease, pain, and cardiovascular disorders such as cardiac failure and heart arrhythmia.

In another aspect, the invention relates to pharmaceutical compositions containing a therapeutically effective amount of at least one compound of formula (I), and their derivatives, prodrugs, tautomers, stereo isomers, polymorphs, solvates, hydrates, metabolites, N-oxides and pharmaceutically acceptable salts thereof, in admixture with at least one suitable carrier, diluents, adjuvants or excipients.

In another aspect, the invention also provides a radio labeled compound of formula (I) for use in medical diagnosis or therapy, as well as the use of a radio labeled compound of formula (I) to prepare a medicament useful in the treatment of various disorders that are related to 5-HT$_4$ receptors.

In another aspect, the invention relates to the use of a compound according to the present invention in combination with at least one further active ingredient for manufacture of a medicament for the treatment/prevention of above mentioned diseases and conditions.

In still another aspect, the invention relates to compositions comprising and methods for using compounds of formula (I).

In yet another aspect, the invention further relates to the process for preparing compounds of formula (I) and their derivatives, prodrugs, tautomers, stereo isomers, polymorphs, solvates, hydrates, metabolites, N-oxides and pharmaceutically acceptable salts.

Representative compounds of the present invention include those specified below and their derivatives, prodrugs, tautomers, stereoisomers, polymorphs, solvates, hydrates, metabolites, N-oxides and pharmaceutically acceptable salts. The present invention should not be construed to be limited to them.

N-[(2-Azatricyclo[3.3.1.1$^{3,7}$]dec-2-yl)propyl]-4-hydroxy-1-isopropyl-2-oxo-1,2-dihydroquinoline-3-carboxamide hydrochloride;

N-[(2-Azatricyclo[3.3.1.1$^{3,7}$]dec-2-yl)propyl]-4-hydroxy-1-isobutyl-2-oxo-1,2-dihydroquinoline-3-carboxamide hydrochloride;

N-[1-(Tricyclo[3.3.1.1$^{3,7}$]dec-2-yl)pyrrolidin-3-yl]-4-hydroxy-1-isopropyl-2-oxo-1,2-dihydroquinoline-3-carboxamide;

N-[(5-Hydroxy-2-azatricyclo[3.3.1.1$^{3,7}$]dec-2-yl)propyl]-4-hydroxy-1-isopropyl-2-oxo-1,2-dihydroquinoline-3-carboxamide;

N-[(5-Phenyl-2-azatricyclo[3.3.1.1$^{3,7}$]dec-2-yl)propyl]-4-hydroxy-1-isopropyl-2-oxo-1,2-dihydroquinoline-3-carboxamide hydrochloride;

N-[(1,4-Diazatricyclo[4.3.1.1$^{3,8}$]undec-4-yl)propyl]-4-hydroxy-1-isopropyl-2-oxo-1,2-dihydroquinoline-3-carboxamide;

N-[(2-Azatricyclo[3.3.1.1$^{3,7}$]dec-2-yl)propyl]-4-hydroxy-1-isobutyl-6-methoxy-2-oxo-1,2-dihydroquinoline-3-carboxamide;

N-[(2-Azatricyclo[3.3.1.1$^{3,7}$]dec-2-yl)propyl]-6-chloro-4-hydroxy-1-isopropyl-2-oxo-1,2-dihydroquinoline-3-carboxamide;

N-[(2-Azatricyclo[3.3.1.1$^{3,7}$]dec-2-yl)propyl]-6-fluoro-4-hydroxy-1-isopropyl-2-oxo-1,2-dihydroquinoline-3-carboxamide;

N-[(2-Azatricyclo[3.3.1.1$^{3,7}$]dec-2-yl)propyl]-6-bromo-4-hydroxy-1-isopropyl-2-oxo-1,2-dihydroquinoline-3-carboxamide;

N-[(2-Azatricyclo[3.3.1.1$^{3,7}$]dec-2-yl)propyl]-6-amino-4-hydroxy-1-isopropyl-2-oxo-1,2-dihydroquinoline-3-carboxamide;

N-[2-(Pyridin-3-ylmethyl)-1-azabicyclo[2.2.2]oct-3-yl]-4-hydroxy-1-isopropyl-2-oxo-1,2-dihydroquinoline-3-carboxamide;

N-[2-(Pyridin-2-ylmethyl)-1-azabicyclo[2.2.2]oct-3-yl]-4-hydroxy-1-isopropyl-2-oxo-1,2-dihydroquinoline-3-carboxamide;

N-(2-Methyl-2-azatricyclo[3.3.1.1$^{3,7}$]dec-5-yl)-4-hydroxy-1-isopropyl-2-oxo-1,2-dihydroquinoline-3-carboxamide;

N-(2-Isopropyl-2-azatricyclo[3.3.1.1$^{3,7}$]dec-5-yl)-4-hydroxy-1-isopropyl-2-oxo-1,2-dihydroquinoline-3-carboxamide;

N-(2-Benzyl-1-azabicyclo[2.2.2]oct-3-yl)-4-hydroxy-1-isopropyl-2-oxo-1,2-dihydroquinoline-3-carboxamide;

N-[(2-Azatricyclo[3.3.1.1$^{3,7}$]dec-2-yl)ethyl]-4-hydroxy-1-isopropyl-2-oxo-1,2-dihydroquinoline-3-carboxamide hydrochloride;

N-(2-Butyl-2-azatricyclo[3.3.1.1$^{3,7}$]dec-5-yl)-4-hydroxy-1-isopropyl-2-oxo-1,2-dihydroquinoline-3-carboxamide hydrochloride;

N-(2-Ethyl-2-azatricyclo[3.3.1.1$^{3,7}$]dec-5-ylmethyl)-4-hydroxy-1-isopropyl-2-oxo-1,2-dihydroquinoline-3-carboxamide hydrochloride;

N-(1-Butylpiperidin-4-yl)-4-hydroxy-1-isopropyl-2-oxo-1,2-dihydroquinoline-3-carboxamide hydrochloride;

N-[(1-(Pyrrolidin-1-yl)tricyclo[3.3.1.0$^{3,7}$]nonan-3-yl]-4-hydroxy-1-isopropyl-2-oxo-1,2-dihydroquinoline-3-carboxamide;

N-[(2-Azatricyclo[3.3.1.1$^{3,7}$]dec-2-yl)propyl]-6-nitro-4-hydroxy-1-isopropyl-2-oxo-1,2-dihydroquinoline-3-carboxamide;

N-(2-Azatricyclo[3.3.1.1$^{3,7}$]dec-5-yl)-4-hydroxy-1-isopropyl-2-oxo-1,2-dihydroquinoline-3-carboxamide hydrochloride;

N-[(2-Azatricyclo[3.3.1.1$^{3,7}$]dec-2-yl)propyl]-4-hydroxy-1-methyl-2-oxo-1,2-dihydroquinoline-3-carboxamide hydrochloride;

N-[(2-Azatricyclo[3.3.1.1$^{3,7}$]dec-2-yl)propyl]-1-benzyl-4-hydroxy-2-oxo-1,2-dihydroquinoline-3-carboxamide hydrochloride;

N-[(4-(Morpholin-4-yl)cyclohexyl)-4-hydroxy-1-isopropyl-2-oxo-1,2-dihydroquinoline-3-carboxamide hydrochloride;

N-(4-(Pyrrolidin-1-yl)cyclohexyl)-4-hydroxy-1-isopropyl-2-oxo-1,2-dihydroquinoline-3-carboxamide hydrochloride;

N-(2-Methyl-2-azatricyclo[3.3.1.1$^{3,7}$]dec-5-yl)-4-hydroxy-1-isopropyl-2-oxo-1,2-dihydroquinoline-3-carboxamide;

N-(2-Methyl-2-azatricyclo[3.3.1.1$^{3,7}$]dec-5-yl)-1-cyclopropyl-4-hydroxy-2-oxo-1,2-dihydroquinoline-3-carboxamide;

N-(2-Methyl-2-azatricyclo[3.3.1.1$^{3,7}$]dec-5-yl)-4-hydroxy-1-isobutyl-2-oxo-1,2-dihydroquinoline-3-carboxamide;

N-[2-(Pyridin-2-ylmethyl)-1-azabicyclo[2.2.2]oct-3-yl]-4-hydroxy-1-isopropyl-2-oxo-1,2-dihydroquinoline-3-carboxamide;

N-[2-(Pyridin-2-ylmethyl)-1-azabicyclo[2.2.2]oct-3-yl]-1-cyclopropyl-4-hydroxy-2-oxo-1,2-dihydroquinoline-3-carboxamide;

N-[2-(Pyridin-2-ylmethyl)-1-azabicyclo[2.2.2]oct-3-yl]-4-hydroxy-1-isobutyl-2-oxo-1,2-dihydroquinoline-3-carboxamide;

N-[(2-Azatricyclo[3.3.1.1$^{3,7}$]dec-2-yl)propyl]-1-cyclopropyl-4-hydroxy-2-oxo-1,2-dihydroquinoline-3-carboxamide;

N-[(2-Azatricyclo[3.3.1.1$^{3,7}$]dec-2-yl)propyl]-1-benzyl-4-hydroxy-2-oxo-1,2-dihydroquinoline-3-carboxamide;

N-[(2-Azatricyclo[3.3.1.1$^{3,7}$]dec-2-yl)propyl]-4-hydroxy-2-oxo-1-(pyridin-2-ylmethyl)-1,2-dihydroquinoline-3-carboxamide;

N-[(2-Azatricyclo[3.3.1.1$^{3,7}$]dec-2-yl)propyl]-4-hydroxy-2-oxo-1-(pyridin-3-ylmethyl)-1,2-dihydroquinoline-3-carboxamide;

N-[(2-Azatricyclo[3.3.1.1$^{3,7}$]dec-2-yl)propyl]-1-cyclopentyl-4-hydroxy-2-oxo-1,2-dihydroquinoline-3-carboxamide;

N-[(2-Azatricyclo[3.3.1.1$^{3,7}$]dec-2-yl)propyl]-1-cyclohexyl-4-hydroxy-2-oxo-1,2-dihydroquinoline-3-carboxamide;

N-[(5-Hydroxy-2-azatricyclo[3.3.1.1$^{3,7}$]dec-2-yl)propyl]-1-cyclohexyl-4-hydroxy-2-oxo-1,2-dihydroquinoline-3-carboxamide;

N-[(5-Hydroxy-2-azatricyclo[3.3.1.1$^{3,7}$]dec-2-yl)propyl]-4-hydroxy-1-isobutyl-2-oxo-1,2-dihydroquinoline-3-carboxamide;

N-[(5-Hydroxy-2-azatricyclo[3.3.1.1$^{3,7}$]dec-2-yl)propyl]-1-cyclopropyl-4-hydroxy-2-oxo-1,2-dihydroquinoline-3-carboxamide;

N-[(5-Hydroxy-2-azatricyclo[3.3.1.1$^{3,7}$]dec-2-yl)propyl]-1-cyclopentyl-4-hydroxy-2-oxo-1,2-dihydroquinoline-3-carboxamide;

N-[(5-Hydroxy-2-azatricyclo[3.3.1.1$^{3,7}$]dec-2-yl)propyl]-4-hydroxy-2-oxo-1-(tetrahydropyran-4-yl)-1,2-dihydroquinoline-3-carboxamide;

N-[(2-Azatricyclo[3.3.1.1$^{3,7}$]dec-2-yl)propyl]-4-hydroxy-2-oxo-1-(tetrahydropyran-4-yl)-1,2-dihydroquinoline-3-carboxamide;

N-[(5-Hydroxy-2-azatricyclo[3.3.1.1$^{3,7}$]dec-2-yl)propyl]-1-benzyl-4-hydroxy-2-oxo-1,2-dihydroquinoline-3-carboxamide;

N-[(5-Hydroxy-2-azatricyclo[3.3.1.1$^{3,7}$]dec-2-yl)propyl]-4-hydroxy-2-oxo-1-(pyridin-2-ylmethyl)-1,2-dihydroquinoline-3-carboxamide;

N-[(5-Phenyl-2-azatricyclo[3.3.1.1$^{3,7}$]dec-2-yl)propyl]-4-hydroxy-2-oxo-1-(pyridin-2-ylmethyl)-1,2-dihydroquinoline-3-carboxamide N-[(5-Phenyl-2-azatricyclo[3.3.1.1$^{3,7}$]dec-2-yl)propyl]-1-cyclopropyl-4-hydroxy-2-oxo-1,2-dihydroquinoline-3-carboxamide;

N-[(5-Phenyl-2-azatricyclo[3.3.1.1$^{3,7}$]dec-2-yl)propyl]-4-hydroxy-1-isobutyl-2-oxo-1,2-dihydroquinoline-3-carboxamide;

N-[(5-Phenyl-2-azatricyclo[3.3.1.1$^{3,7}$]dec-2-yl)propyl]-4-hydroxy-2-oxo-1-(2-methylbenzyl)-1,2-dihydroquinoline-3-carboxamide;

N-[1-(Tetrahydropyran-4-ylmethyl)piperidin-4-yl]-4-hydroxy-1-isopropyl-2-oxo-1,2-dihydroquinoline-3-carboxamide;

N-[1-(Tetrahydropyran-4-ylmethyl)piperidin-4-yl]-1-cyclopropyl-4-hydroxy-2-oxo-1,2-dihydroquinoline-3-carboxamide;

N-[1-(Tetrahydropyran-4-ylmethyl)piperidin-4-yl]-4-hydroxy-1-isobutyl-2-oxo-1,2-dihydroquinoline-3-carboxamide;

N-[1-(Tetrahydropyran-4-ylmethyl)piperidin-4-yl]-1-benzyl-4-hydroxy-2-oxo-1,2-dihydroquinoline-3-carboxamide;

N-(1-Phenethyl piperidin-4-yl)-4-hydroxy-1-isopropyl-2-oxo-1,2-dihydroquinoline-3-carboxamide;

N-[(1-(Pyrrolidin-1-yl)tricyclo[3.3.1.0$^{3,7}$]nonan-3-yl]-1-cyclopropyl-4-hydroxy-2-oxo-1,2-dihydroquinoline-3-carboxamide;

N-[(1-(Pyrrolidin-1-yl)tricyclo[3.3.1.0$^{3,7}$]nonan-3-yl]-1-cyclohexyl-4-hydroxy-2-oxo-1,2-dihydroquinoline-3-carboxamide;

N-[(1-(Pyrrolidin-1-yl)tricyclo[3.3.1.0$^{3,7}$]nonan-3-yl]-1-benzyl-4-hydroxy-2-oxo-1,2-dihydroquinoline-3-carboxamide;

N-[(1-(Pyrrolidin-1-yl)tricyclo[3.3.1.0$^{3,7}$]nonan-3-yl]-4-hydroxy-2-oxo-1-(pyridin-2-ylmethyl)-1,2-dihydroquinoline-3-carboxamide;

N-[(1-(Pyrrolidin-1-yl)tricyclo[3.3.1.0$^{3,7}$]nonan-3-yl]-4-hydroxy-1-isopropyl-2-oxo-1,2-dihydroquinoline-3-carboxamide;

N-[(1-(Pyrrolidin-1-yl)tricyclo[3.3.1.0$^{3,7}$]nonan-3-yl]-1-cyclopropyl-4-hydroxy-2-oxo-1,2-dihydroquinoline-3-carboxamide;

N-[(1-(Pyrrolidin-1-yl)tricyclo[3.3.1.0$^{3,7}$]nonan-3-yl]-1-cyclohexyl-4-hydroxy-2-oxo-1,2-dihydroquinoline-3-carboxamide;

N-(2-Methyl-2-azatricyclo[3.3.1.1$^{3,7}$]dec-5-ylmethyl)-4-hydroxy-1-isopropyl-2-oxo-1,2-dihydroquinoline-3-carboxamide;

N-(2-Methyl-2-azatricyclo[3.3.1.1$^{3,7}$]dec-5-ylmethyl)-1-cyclopropyl-4-hydroxy-2-oxo-1,2-dihydroquinoline-3-carboxamide;

N-(2-Methyl-2-azatricyclo[3.3.1.1$^{3,7}$]dec-5-ylmethyl)-1-benzyl-4-hydroxy-2-oxo-1,2-dihydroquinoline-3-carboxamide;

N-(2-Methyl-2-azatricyclo[3.3.1.1$^{3,7}$]dec-5-ylmethyl)-4-hydroxy-1-isobutyl-2-oxo-1,2-dihydroquinoline-3-carboxamide;

N-(2-Methyl-2-azatricyclo[3.3.1.1$^{3,7}$]dec-5-ylmethyl)-1-cyclohexyl-4-hydroxy-2-oxo-1,2-dihydroquinoline-3-carboxamide;

N-(2-Ethyl-2-azatricyclo[3.3.1.1$^{3,7}$]dec-5-ylmethyl)-1-cyclopentyl-4-hydroxy-2-oxo-1,2-dihydroquinoline-3-carboxamide;

N-[(5-Methoxy-2-azatricyclo[3.3.1.1$^{3,7}$]dec-2-yl)propyl]-4-hydroxy-1-isopropyl-2-oxo-1,2-dihydroquinoline-3-carboxamide and N-[(5-Butoxy-2-azatricyclo[3.3.1.1$^{3,7}$]dec-2-yl)propyl]-4-hydroxy-1-isopropyl-2-oxo-1,2-dihydroquinoline-3-carboxamide.

DETAILED DESCRIPTION OF THE INVENTION

Unless otherwise stated, the following terms used in the specification and claims have the meanings given below:

The term "halogen" means fluorine, chlorine, bromine or iodine.

The term "alkyl" means straight chain or branched hydrocarbon radical consisting solely of carbon and hydrogen atoms, containing no unsaturation, having from one to eight carbon atoms, and which is attached to the rest of the molecule by a single bond. Exemplary "alkyl" groups include methyl, ethyl, n-propyl, iso-propyl and the like.

The term "alkenyl" means straight chain or branched aliphatic hydrocarbon group containing a carbon-carbon double bond and having 2 to 10 carbon atoms. Exemplary "Alkenyl" groups include ethenyl, 1-propenyl, 2-propenyl(allyl), isopropenyl, 2-methyl-1-propenyl, 1-butenyl, 2-butenyl and the like.

The term "alkynyl" means straight chain or branched hydrocarbynyl radical having at least one carbon-carbon triple bond and having 2 to 10 carbon atoms. Exemplary "alkynyl" groups include ethynyl, propynyl, butynyl and the like.

The term "alkoxy" means an alkyl group attached via an oxygen linkage to the rest of the molecule. Exemplary "alkoxy" groups include methoxy, ethoxy, propyloxy, iso-propyloxy and the like.

The term "cycloalkyl" means non-aromatic mono or multi cyclic ring systems of 3 to 12 carbon atoms. Exemplary "cycloalkyl" groups include cyclopropyl, cyclobutyl, cyclopenty and the like.

The term "haloalkyl" means straight or branched chain alkyl radicals containing one to three carbon atoms. Exemplary "haloalkyl" groups include fluoromethyl, difluoromethyl, trifluoromethyl, trifluoroethyl, fluoroethyl, difluoroethyl and the like.

The term "haloalkoxy" means straight or branched chain alkoxy radicals containing one to three carbon atoms. Exemplary "haloalkoxy" groups include fluoromethoxy, difluoromethoxy, trifluoromethoxy, trifluoroethoxy, fluoroethoxy, difluoroethoxy and the like.

The term "aryl" means any functional group or substituent derived from a simple aromatic ring, Exemplary "aryl" groups include phenyl, naphthyl, thiophenyl, indolyl, and the like.

The term "aralkyl" means aralkyl ring radical directly bonded to an alkyl group.

The term "heteroaryl" means organic compounds that contain a ring structure containing atoms in addition to carbon such as sulfur, oxygen or nitrogen, as part of the ring. These additional atoms may be repeated more than once in ring. These rings may be either simple aromatic rings or non-aromatic rings Exemplary "heteroaryl" groups include pyridine, pyrimidine, benzothiophene, furyl, dioxalanyl, pyrrolyl, oxazolyl, pyridyl, pyridazinyl, pyrimidinyl and the like.

The term "heteroaralkyl" means heteroaryl ring radical directly bonded to an alkyl group.

The term "heterocyclyl" means 3 to 12-membered rings, whose ring structures include 1 to 3 heteroatoms; these additional atoms may be repeated more than once in ring. Exemplary "Heterocyclyl" groups include pyrrolidinyl, piperidinyl, morpholinyl and the like.

The following groups may be substituted or unsubstituted, they are cycloalkyl, aryl, aralkyl, heteroaralkyl, heteroaryl and heterocyclyl. Optionally substituents on these groups may be selected from the group consisting of hydrogen, hydroxy, halogen, nitro, thio, oxo, carboxylic, amine, amide, alkyl, alkoxy, haloalkyl or haloalkoxy.

The term "stereo isomers" is a general term for all isomers of the individual molecules that differ only in the orientation of their atoms in space. It includes mirror image isomers (enantiomers), geometric (cis-trans) isomers and isomers of compounds with more than one chiral centre that are not mirror images of one another (diastereomers).

The term "prodrug" is used to refer to a compound capable of converting, either directly or indirectly, into compounds described herein by the action of enzymes, gastric acid and the like under in vivo physiological conditions (e.g., enzymatic oxidation, reduction and/or hydrolysis).

The term "solvate" is used to describe a molecular complex between compounds of the present invention and solvent molecules. Examples of solvates include, but are not limited to, compounds of the invention in combination with water, isopropanol, ethanol, methanol, dimethylsulfoxide (DMSO), ethyl acetate, acetic acid, ethanolamine or mixtures thereof.

The term "hydrate" can be used when said solvent is water. It is specifically contemplated that in the present invention one solvent molecule can be associated with one molecule of the compounds of the present invention, such as a hydrate. Furthermore, it is specifically contemplated that in the present invention, more than one solvent molecule may be associated with one molecule of the compounds of the present invention, such as a dihydrate. Additionally, it is specifically contemplated that in the present invention less than one solvent molecule may be associated with one molecule of the compounds of the present invention, such as a hemihydrate. Furthermore, solvates of the present invention are contemplated as solvates of compounds of the present invention that retain the biological effectiveness of the non-hydrate form of the compounds.

The term "tautomers" include readily interconvertible isomeric forms of a compound in equilibrium. The enol-keto tautomerism is an example.

The term "polymorphs" include crystallographically distinct forms of compounds with chemically identical structures.

The term "metabolite" refers to substance produced by metabolism.

The term "derivative" refers to a compound obtained from a compound according to formula (I), and their tautomers, stereoisomers, polymorphs, solvates, hydrates, N-oxides and pharmaceutically acceptable salts thereof, by a simple chemical process converting one or more functional groups such as by oxidation, hydrogenation, alkylation, esterification, halogenation and the like.

The terms "treating", "treat" or "treatment" embrace all the meanings such as preventative, prophylactic and palliative.

The phrase "pharmaceutically acceptable salts" indicates that the substance or composition must be compatible chemically and/or toxicologically, with the other ingredients comprising a formulation, the mammal being treated therewith.

The phrase "Therapeutically effective amount" is defined as 'an amount of a compound of the present invention that (i) treats or prevents the particular disease, condition or disorder (ii) attenuates, ameliorates or eliminates one or more symptoms of the particular disease, condition or disorder (iii) prevents or delays the onset of one or more symptoms of the particular disease, condition or disorder described herein'.

The term "modulator" means compounds, agonists, antagonists, ligands, substrates and enzymes which directly or indirectly affect the regulation of the receptor activity.

Commercial reagents were utilized without further purification. Room temperature refers to 25-30° C. IR were taken using KBr and in solid state. Unless otherwise stated, all mass spectra were carried out using ESI conditions. $^1$H-NMR spectra were recorded at 400 MHz on a Bruker instrument. Deuterated chloroform (99.8% D) was used as solvent. TMS was used as internal reference standard. Chemical shift values are expressed in parts per million (δ) values. The following abbreviations are used for the multiplicity for the NMR signals: s=singlet, bs=broad singlet, d=doublet, t=triplet, q=quartet, qui=quintet, h=heptet, dd=double doublet, dt=double triplet, tt=triplet of triplets, m=multiplet. Chromatography refers to column chromatography performed using 100-200 mesh silica gel and executed under nitrogen pressure (flash chromatography) conditions.

The compounds of the invention can be used in combination, with other therapeutic agents or approaches used to treatment/prevention the conditions as mentioned above. Such agents or approaches include 5-HT$_3$ receptors, 5-HT$_6$ receptors, proton pump inhibitors, selective serotonin reuptake inhibitors, tricyclic antidepressants, cholecystokinin receptors, motilin receptors, nitric oxide synthase inhibitors, GABA$_B$ receptor agonists or modulators, Neurokinin receptors, calcitonin gene-related peptide receptors, stimulant laxatives, osmotic laxatives, fecal softeners, fiber supplements, antacids, GI relaxants, loperamide, diphenoxylate, anti-gas compounds, anti-emetic dopamine D2 antagonists, mast-cell stabilizing agents, DPP IV inhibitors, acholinesterase inhibitors, α2-adrenoceptor antagonists, NMDA receptor antagonists, M1 muscarinic receptor agonists, allosteric modulators, histamine H$_2$ receptor antagonists, histamine H$_3$ receptor antagonists, Xanthin derivatives, calcium channel blockers, prostaglandin analogues, opioid analgesics, somatostatin analogues or Cl channel activators.

In the combination of the present invention, the compounds of the present invention and the above mentioned combination partners may be administered separately (e.g. kit of parts) or together in, one pharmaceutical composition (e.g. capsule or tablet). In addition, the administration of one element of the combination of the present invention may be prior to, concurrent to, or subsequent to the administration of the other element of the combination. If the compounds of the present invention and the one or more additional active ingredient are present in, separate formulations these separate formulations, may be administered simultaneously or sequentially.

For the treatment or prevention of the above mentioned diseases and conditions compounds of the invention can be used in combination with immunological approaches, such as, for example, immunization with A beta peptide or derivatives thereof or administration of anti-A beta peptide antibodies.

Therefore, the invention relates to the use of a compound according to the present invention in combination with at least one further active ingredient for the manufacture of a medicament for the treatment or prevention of diseases and conditions mentioned earlier.

Numerous radioisotopes are readily available including isotopes of hydrogen, carbon, nitrogen, oxygen, phosphorus, sulfur, iodine, fluorine, bromine & chlorine. For example: $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{123}$I, $^{124}$I, $^{125}$I, $^{131}$I, $^{18}$F, $^{75}$Br, $^{76}$Br, $^{77}$Br, $^{82}$Br & $^{36}$Cl.

A compound of general formula (I) can be radio labeled by using standard techniques known in organic chemistry. Alternatively, compound of formula (I) radio labeled with radioisotope as a substituent in one of the starting materials or in an intermediate used in the synthesis of the compound of formula (I). For example, see Arthur Murry III, D. Lloyd Williams; Organic Synthesis with Isotopes, vol. I and II, Interscience Publishers Inc., N.Y. (1958) and Melvin Calvin et al. Isotopic Carbon John Wiley and Sons Inc., N.Y. (1949).

Synthesis of radio labeled compounds may be conveniently performed by a radioisotope supplier specializing in custom synthesis of radio labeled probe compounds, such as Amersham Corporation, Arlington Heights, Ill.; Cambridge Isotopes Laboratories, Inc. Andover, Mass.; Wizard Laboratories, West Sacramento, Calif.; ChemSyn Laboratories, Lexena, Kans.; American Radiolabeled Chemicals, Inc. & St. Louis, Mo.;

Radio labeled analogues of compound of formula (I) may be used in clinical studies to evaluate the role of 5-HT$_4$ receptor ligands in a variety of disease areas, where 5-HT$_4$ receptor ligands are believed to be involved.

Radio labeled compounds of formula (I) are useful as imaging agents and biomarker for medical therapy and diagnosis. Such radiolabeled compounds are also useful as pharmacological tools for studying 5-HT$_4$ functions and activity. For example, isotopically labeled compounds are particularly useful in SPECT (single photon emission compound tomography) and in PET (positron emission tomography).

Pharmaceutical Compositions

In order to use the compounds of formula (I) in therapy, they will normally be formulated into a pharmaceutical composition in accordance with standard pharmaceutical practice.

The pharmaceutical compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or a form suitable for administration by inhalation or insufflations.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol) and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of an aerosol spray from a pressurized container or a nebulizer or from a capsule using a inhaler or insufflators. In the case of a pressurized aerosol, a suitable propellant, e.g., dichlorodifluoromethane, trichlorofluoromethane, dichlorotetrafluoroethane, carbon dioxide or other suitable gas and the dosage unit may be determined by providing a valve to deliver a metered amount. The medicament for pressurized container or nebulizer may contain a solution or suspension of the active compound while for a capsule; it preferably should be in the form of powder. Capsules and cartridges (made, for example, from gelatin) for use in an inhaler or insufflator may be formulated containing a powder mix of a compound of the invention and a suitable powder base such as lactose or starch.

Aerosol formulations for treatment of the conditions referred to above (e.g., migraine) in the average adult human are preferably arranged so that each metered dose or "puff" of aerosol contains 20 μg to 1000 μg of the compound of the invention. The overall daily dose with an aerosol will be within the range 100 μg to 10 mg. Administration may be several times daily, for example 2, 3, 4 or 8 times, giving for example, 1, 2 or 3 doses each time.

An effective amount of a compound of general formula (I) or their derivatives as defined above can be used to produce a medicament, along with conventional pharmaceutical auxiliaries, carriers and additives.

Such a therapy includes multiple choices: for example, administering two compatible compounds simultaneously in a single dose form or administering each compound individually in a separate dosage; or if required at same time interval or separately in order to maximize the beneficial effect or minimize the potential side-effects of the drugs according to the known principles of pharmacology.

The dose of the active compounds can vary depending on factors such as the route of administration, age and weight of patient, nature and severity of the disease to be treated and similar factors. Therefore, any reference herein to a pharmacologically effective amount of the compounds of general formula (I) refers to the aforementioned factors. A proposed dose of the active compounds of this invention, for either oral, parenteral, nasal or buccal administration, to an average adult human, for the treatment of the conditions referred to above, is 0.1 to 200 mg of the active ingredient per unit dose which could be administered, for example, 1 to 4 times per day.

The present invention provides compounds and pharmaceutical formulation thereof that are useful in the treatment/ prevention of various disorders that are related to 5-$HT_4$ receptors.

Method of Preparation

The compounds of formula (I) can be prepared by Scheme I as shown below

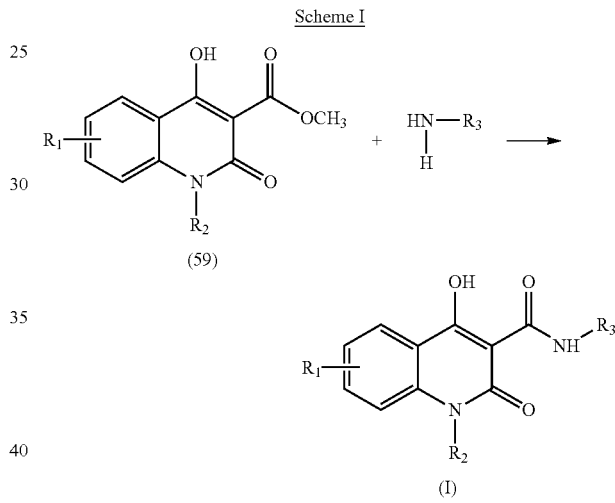

The process of this invention includes, reaction of ester compound of formula (59) with amine compound, using suitable solvent to obtain a compound of formula (I), wherein all substitutions are described as earlier.

The solvent used in above reaction is selected from group consisting of as ethanol, tetrahydrofuran, dichloromethane, dichloroethane, toluene, dimethylformamide, dimethyl sulfoxide and the like or a mixture thereof and preferably by using toluene. The base may be or may not used in above reaction. If base is used, the base in above reaction is selected from the group consisting of sodium hydroxide, potassium hydroxide, sodium carbonate, potassium carbonate and aqueous ammonia. In absence of base, the duration of the reaction may range from 1 to 5 hours, preferably from a period of 2 to 3 hours. In presence of base the duration of the reaction may range from 15 to 20 hours, preferably from a period of 16 to 19 hours.

The compound of formula (59) is synthesized as described in preparation 10. The amine compounds are prepared by experimental procedures as mentioned in preparations 1 to 9.

Compounds obtained by the above method of preparation of the present invention can be transformed into another compound of this invention by further chemical modifications using well-known reactions such as oxidation, reduction, protection, deprotection, rearrangement reaction, halogenation, hydroxylation, alkylation, alkylthiolation, demethylation, O-alkylation, O-acylation, N-alkylation, N-alkenylation, N-acylation, N-cyanation, N-sulfonylation, coupling reaction using transition metals and the like.

If necessary, any one or more than one of the following steps can be carried out, i) Converting a compound of the formula (I) into another compound of the formula (I)

ii) Removing any protecting groups; or iii) Forming a pharmaceutically acceptable salt, solvate or a prodrug thereof.

Process (i) may be performed using conventional interconversion procedures such as epimerisation, oxidation, reduction, alkylation, and nucleophilic or electrophilic aromatic substitution and ester hydrolysis or amide bond formation.

In process (ii) examples of protecting groups and the means for their removal can be found in T. W. Greene 'Protective Groups in Organic Synthesis' (J. Wiley and Sons, 1991). Suitable amine protecting groups include sulfonyl (e.g. tosyl), acyl (e.g. acetyl, 2',2',2'-trichloroethoxycarbonyl, benzyloxycarbonyl or t-butoxycarbonyl) and arylalkyl (eg. benzyl), which may be removed by hydrolysis (e.g. using an acid such as hydrochloric or trifluoroacetic acid) or reductively (e.g. hydrogenolysis of a benzyl group or reductive removal of a 2',2',2'-trichloroethoxycarbonyl group using zinc in acetic acid) as appropriate. Other suitable amine protecting groups include trifluoroacetyl, which may be removed by base catalyzed hydrolysis or a solid phase resin bound benzyl group, such as a Merrifield resin bound 2,6-dimethoxybenzyl group (Ellman linker), which may be removed by acid catalyzed hydrolysis, for example with trifluoroacetic acid.

In process (iii) pharmaceutically acceptable salts may be prepared conventionally by reaction with the appropriate acid or acid derivative as described earlier in detail. Solvates may be prepared by treating with the appropriate solvents and prodrugs may be prepared by further chemical transformations like alkylation's, esterifications etc.

Certain compounds of formula (I) are capable of existing in stereoisomeric forms (e.g. diastereomers and enantiomers) and the invention extends to each of these stereoisomeric forms and to mixtures thereof including racemates. The different stereoisomeric forms may be separated from one another by the usual methods like resolutions; diastereoisomeric separations etc or any given isomer may be obtained by stereospecific or asymmetric synthesis. The invention also extends to tautomeric forms and mixtures thereof.

The stereoisomers as a rule are generally obtained as racemates that can be separated into the optically active isomers in a manner known per se. In the case of the compounds of general formula (I) having an asymmetric carbon atom the present invention relates to the D-form, the L-form and D,L-mixtures and in the case of compound of general formula (I) containing a number of asymmetric carbon atoms, the diastereomeric forms and the invention extends to each of these stereo isomeric forms and to mixtures thereof including racemates. Those compounds of general formula (I) which have an asymmetric carbon and as a rule are obtained as racemates can be separated one from the other by the usual methods, or any given isomer may be obtained by stereo specific or asymmetric synthesis. However, it is also possible to employ an optically active compound from the start, a correspondingly optically active enantiomeric or diastereomeric compound then being obtained as the final compound.

The stereoisomers of compounds of general formula (I) may be prepared by one or more ways presented below:

i) One or more of the reagents may be used in their optically active form.

ii) Optically pure catalyst or chiral ligands along with metal catalyst may be employed in the reduction process. The metal catalyst may be Rhodium, Ruthenium, Indium and the like. The chiral ligands may preferably be chiral phosphines (Principles of Asymmetric synthesis, J. E. Baldwin Ed., Tetrahedron series, 14, 311-316).

iii) The mixture of stereoisomers may be resolved by conventional methods such as forming diastereomeric salts with chiral acids or chiral amines or chiral amino alcohols, chiral amino acids. The resulting mixture of diastereomers may then be separated by methods such as fractional crystallization, chromatography and the like, which is followed by an additional step of isolating the optically active product by hydrolyzing the derivative or by neutralization reaction (Jacques et. al., "Enantiomers, Racemates and Resolution", Wiley Interscience, 1981).

iv) The mixture of stereoisomers may be resolved by conventional methods such as microbial resolution, resolving the diastereomeric salts formed with chiral acids or chiral bases.

Chiral acids that can be employed may be tartaric acid, mandelic acid, lactic acid, camphorsulfonic acid, amino acids and the like. Chiral bases that can be employed may be cinchona alkaloids, brucine or a basic amino acid such as lysine, arginine and the like. In the case of the compounds of general formula (I) containing geometric isomerism the present invention relates to all of these geometric isomers.

Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid and organic acids e.g., succinic, maleic, acetic, fumaric, citric, malic, tartaric, benzoic, p-toluic, p-toluenesulfonic, benzenesulfonic acid, methanesulfonic or naphthalenesulfonic acid. The present invention includes, within its scope, all possible stoichiometric and non-stoichiometric forms.

The pharmaceutically acceptable salts forming a part of this invention may be prepared by treating the compound of formula (I) with 1-6 equivalents of a base such as sodium hydride, sodium methoxide, sodium ethoxide, sodium hydroxide, potassium t-butoxide, calcium hydroxide, calcium acetate, calcium chloride, magnesium hydroxide, magnesium chloride and the like. Solvents such as water, acetone, ether, THF, methanol, ethanol, t-butanol, dioxane, isopropanol, isopropyl ether or mixtures thereof may be used.

The compounds of formula (I) may be prepared in crystalline or non-crystalline form and if crystalline, may optionally be solvated, eg. as the hydrate. This invention includes within its scope stoichiometric solvates (eg. hydrates) as well as compounds containing variable amounts of solvent (eg. water).

Various polymorphs of compound of general formula (I) forming part of this invention may be prepared by crystallization of compound of formula (I), under different conditions. For example, using different solvents commonly used or their mixtures for recrystallization, crystallizations at different temperatures; various modes of cooling ranging from very fast to very slow cooling during crystallizations. Polymorphs may also be obtained by gradual or fast cooling of compound after heating or melting. The presence of polymorphs may be determined by solid probe NMR spectroscopy, IR spectroscopy, differential scanning calorimetry, powder X-ray diffraction or such other techniques.

Pharmaceutically acceptable solvates of the compounds of formula (I) forming part of this invention may be prepared by conventional methods such as dissolving the compounds of formula (I) in solvents such as water, methanol, ethanol, mixture of solvents such as acetone-water, dioxane-water, N,N-dimethylformamide-water and the like, preferably water and recrystallizing by using different crystallization techniques.

Prodrugs of the present application may be prepared from compound of formula (I) by using known process. Conventional procedures for the selection and preparation of suitable prodrug derivatives are described, for example, in Design of prodrugs (1985); Wihnan, Biochem Soc. Trans. 1986, 14, 375-82; Stella et al., Prodrugs: A chemical approach to targeted drug delivery in directed drug delivery, 1985, 247-67, each of which is incorporated by reference herein in its entirety.

Tautomers of compounds of formula (I) can be prepared by using known process. Procedures for preparation of suitable Tautomers are described, for example in Smith M B, March J (2001). Advanced Organic Chemistry (5th ed.) New York: Wiley Interscience. pp. 1218-1223 and Katritzky A R, Elguero J, et al. (1976). The Tautomerism of heterocycles. New York: Academic Press.

N-Oxides of compounds of formula (I) can be prepared by using known process. Procedures for preparation of suitable N-Oxides are described, March's Advanced Organic Chemistry: Reactions, Mechanisms, and Structure Michael B. Smith, Jerry March Wiley-Interscience, 5th edition, 2001.

Hydrates of compounds of formula (I) can be prepared by using known process.

In the case of the compounds of general formula (I) containing geometric isomerism the present invention relates to all of these geometric isomers.

EXAMPLES

The novel compounds of the present invention were prepared according to the following procedures, using appropriate materials and are further exemplified by the following specific examples. The most preferred compounds of the invention are any or all of those specifically set forth in these examples. These compounds are not, however, to be construed as forming the only genus that is considered as the invention and any combination of the compounds or their moieties may itself form a genus. The following examples further illustrate details for the preparation of the compounds of the present invention. Those skilled in the art will readily understand that known variations of the conditions and process of the following preparative procedures can be used to prepare these compounds.

Preparation 1

Preparation of Compound of Formula (8)

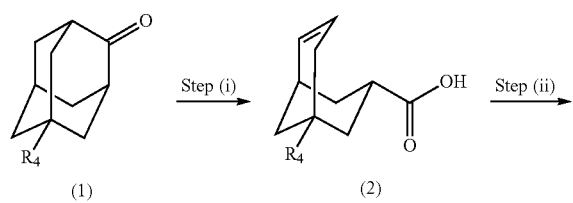

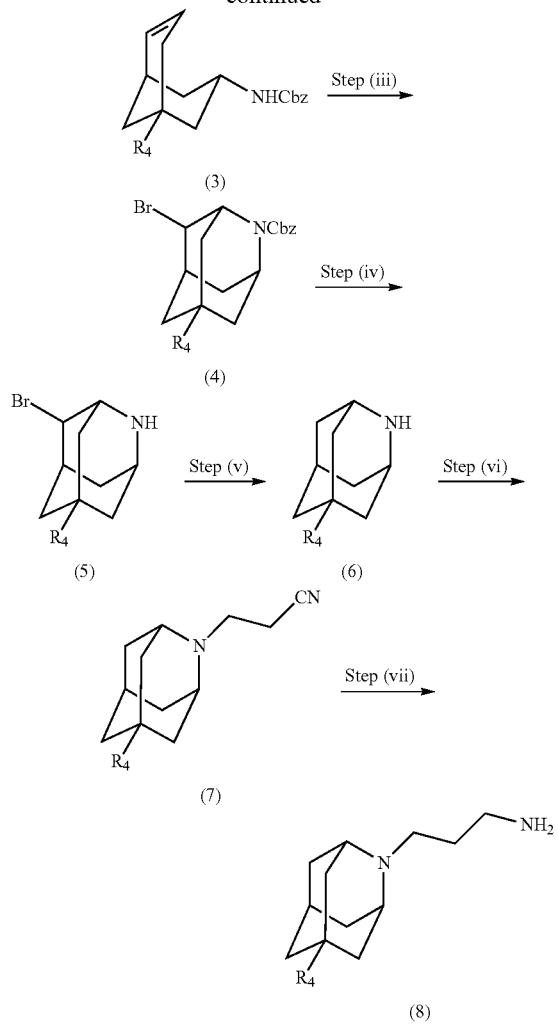

Step (i): Preparation of Compound of Formula (2)

To a stirred solution of compound of formula (I) ($R_4$=H) (20.0 grams, 133.1 mmol) in methanesulfonic acid (125 grams) was added sodium azide (9.0 grams, 39.8 mmol) portion wise over 2 hours. The temperature was maintained at 20-25° C. during the addition. Nitrogen evolution ceased 2 hour after the addition was completed. After stirring an additional hour at room temperature, the reaction solution was diluted with 100 mL of water. An excess of 50% potassium hydroxide solution was carefully added portion wise without external cooling. The exothermic reaction yielded a solution, which was extracted once with ether. The aqueous layer was acidified with concentrated hydrochloric acid. The precipitated organic acid was collected by filtration, washed with five 50 mL portions of distilled water, and then dried in a vacuum desiccator over phosphorus pentoxide to give compound of formula (2) ($R_4$=H) (17.9 grams). Yield: 81%.

Melting Point: 196-198° C.;

$^1$H-NMR (CDCl$_3$): δ 12.2-11.2 (bs, 1H), 5.80-5.50 (m, 2H), 2.62-2.54 (m, 1H), 2.45-1.80 (m, 7H), 1.80-1.65 (m, 2H), 1.60-1.52 (m, 1H).

IR (cm$^{-1}$): 3266, 3022, 2924, 2896, 2632, 1682, 1436, 1411, 1331, 1304, 1268, 1244, 1103, 1008, 965, 935, 872, 714, 616.

Mass (m/z): 167 [M+H$^+$].

Step (ii): Preparation of Compound of Formula (3)

To a stirred solution compound of formula (2) ($R_4$=H) (5 grams, 30.0 mmol) in dichloroethane (50 mL), was added triethylamine (8.3 mL, 60.0 mmol) followed by diphenylphosphoryl azide (7.1 mL, 33 mmol). The reaction mixture was stirred for 30 minutes at room temperature then refluxed for 2 hours. Benzyl alcohol (5.2 mL, 49.9 mmol) was added and refluxed for another 5 hours. The reaction mixture was diluted with chloroform and aqueous sodium bicarbonate solution. The two layers were separated and the organic layer was washed with water, brine, dried over anhydrous sodium sulphate and the solvent was removed under reduced pressure to obtain the crude product which was purified by flash silica gel column which afforded compound of formula (3) ($R_4$=H) (3.24 grams). Yield: 40%.

$^1$H-NMR (CDCl$_3$): δ 7.42-7.27 (m, 5H), 6.12-6.05 (m, 1H), 5.95 (bd, 1H), 5.88-5.75 (m, 1H), 5.06 (dd, J=19.6, 12.3 Hz, 2H), 4.15-4.0 (m, 1H), 2.50-2.30 (m, 2H), 2.25-2.15 (m, 1H), 2.10-1.90 (m, 2H), 1.90-1.67 (m, 4H), 1.62-1.50 (m, 1H).

IR (cm$^{-1}$): 3431, 3364, 3018, 2928, 2145, 1708, 1578, 1507, 1487, 1386, 1216, 1062, 861, 758, 668.

Mass (m/z): 272 [M+H$^+$].

Step (iii): Preparation of Compound of Formula (4)

To a stirred solution of compound of formula (3) ($R_4$=H) (3.2 grams, 11.8 mmol) in carbon tetrachloride (47 mL) cooled at 0° C. was added a solution of bromine in carbon tetrachloride (5% w/v) till orange color persisted. The volatiles were removed under reduced pressure to obtain a crude reaction mixture, which was purified by silica gel flash chromatography to get compound of formula (4) ($R_4$=H) (3.4 grams) and compound of formula (5) ($R_4$=H) (1.32 grams).

$^1$H-NMR (CDCl$_3$): δ 7.42-7.27 (m, 5H), 6.12-6.05 (m, 1H), 5.95 (bd, 1H), 5.88-5.75 (m, 1H), 5.06 (dd, J=19.6, 12.3 Hz, 2H), 4.15-4.0 (m, 1H), 2.50-2.30 (m, 2H), 2.25-2.15 (m, 1H), 2.10-1.90 (m, 2H), 1.90-1.67 (m, 4H), 1.62-1.50 (m, 1H).

IR: 2930, 2857, 2145, 1697, 1585, 1414, 1299, 1101, 1082, 956, 750, 696.

Mass (m/z): 350, 352 [M+H$^+$].

Step (iv): Preparation of Compound of Formula (5)

To a stirred solution of compound of formula (4) ($R_4$=H) (6.5 grams, 18.5 mmol) in isopropanol (10 mL) cooled at 0° C., was added a solution of dry hydrochloride in isopropanol (74 mL). The reaction mixture was stirred at room temperature for 16 hours. The volatiles were removed under reduced pressure to obtain a crude mass, which was triturated with ether to obtain compound of formula (5) ($R_4$=H) (2.4 grams), Yield: 60%.

$^1$H-NMR (CDCl$_3$): δ 9.80-9.40 (bd, 2H), 4.90 (bs, 1H), 3.84 (bs, 1H), 3.81 (bs, 1H), 2.65-2.50 (m, 2H), 2.50-2.20 (m, 4H), 2.20-2.05 (m, 2H), 1.95-1.85 (m, 1H), 1.80-1.70 (m, 1H).

IR: 3420, 2938, 2822, 2473, 2051, 1582, 1464, 1428, 1385, 1360, 1333, 1200, 1109, 1000, 749.

Mass (m/z): 216, 218 [M+H$^+$].

Step (v): Preparation of Compound of Formula (6)

To a stirred solution of compound of formula (5) ($R_4$=H) (4.55 grams, 21 mmol) in dry tetrahydrofuran (42 mL) cooled at 0° C., was added a solution of lithiumaluminium hydride (1M in tetrahydrofuran, 31.5 mL, 31.5 mmol). The reaction mixture was stirred at room temperature for 2 hours before being quenched by adding water (1.2 mL), aqueous sodium hydroxide (15%, 1.23 mL) and water (3.5 mL) in sequence. The reaction mixture was filtered through a small pad of celite, the filtrate was dried over anhydrous sodium sulphate and the solvent was removed under reduced pressure to obtain compound of formula (6) ($R_4$=H) (2.125 grams). Yield: 74%.

$^1$H-NMR (CDCl$_3$): δ 3.19 (bs, 1H), 2.52 (bs, 1H), 2.10-1.95 (m, 6H), 1.90-1.85 (m, 2H), 1.82-1.75 (m, 4H).

Mass (m/z): 138 [M+H$^+$].

Step (vi): Preparation of Compound of Formula (7)

To a stirred solution of compound of formula (6) ($R_4$=H) (2.1 grams, 15.4 mmol) in methanol (31 mL) cooled at 0° C. was added acrylonitrile (1 mL, 15.4 mmol). The reaction mixture was gradually warmed to room temperature and stirred for 16 hours. Upon completion of the reaction, the volatiles were removed under reduced pressure and the crude product was purified by silica gel flash chromatography to obtain compound of formula (7) ($R_4$=H) (2.12 grams). Yield: 73%.

$^1$H-NMR (CDCl$_3$): δ 2.94 (t, J=7.0 Hz, 2H), 2.84 (bs, 2H), 2.44 (t, J=6.9 Hz, 2H), 2.08-1.95 (m, 6H), 1.81 (bs, 2H), 1.70-1.52 (m, 4H).

Mass (m/z): 191 [M+H$^+$].

Step (vii): Preparation of Compound of Formula (8)

To a stirred solution of compound of formula (7) ($R_4$=H) (2.1 grams, 11.04 mmol) in methnolic ammonia (7M, 44 mL) was added Raney-Nickel (40 wt %, 0.84 grams). The reaction mixture was stirred under hydrogen atmosphere (balloon pressure) for 16 hours. The reaction mixture was filtered through celite, the filtrate was dried over anhydrous sodium sulphate and the solvent was removed under reduced pressure to obtain compound of formula (8) ($R_4$=H) (2.14 grams). Yield: 100%.

$^1$H-NMR (CDCl$_3$): δ 3.0-2.70 (m, 6H), 2.15-1.95 (m, 6H), 1.90-1.60 (m, 4H), 1.60-1.50 (m, 4H).

Mass (m/z): 195 [M+H$^+$].

Preparation 2

Preparation of Compound of Formula (10)

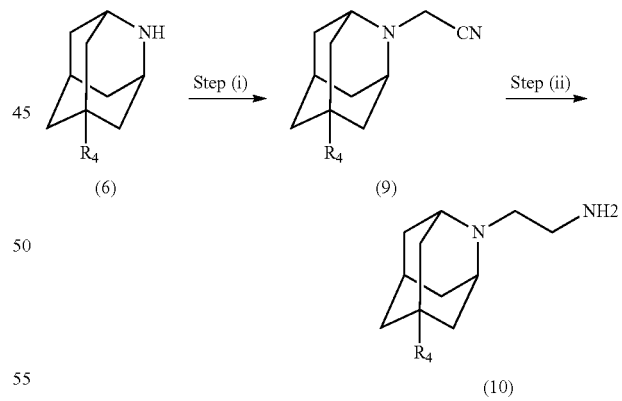

Step (i): Preparation of Compound of Formula (9)

To a stirred mixture compound of formula (6) ($R_4$=H) (0.9 grams, 6.5 mmol), potassium carbonate (1.2 grams, 9.18 mmol) and tetrabutylammonium iodide (242 mg, 0.65 mmol) in acetonitrile (43 mL) was added chloroacetonitrile (0.48 mL, 7.78 mmol). The reaction mixture was refluxed for 5 hours. The volatiles were removed; the residue was diluted with water and extracted with ethylacetate. The combined organic layer was washed with brine, dried over anhydrous sodium sulphate and the solvent was removed under reduced pressure. The crude product was purified by silica gel flash chromatography to obtain the compound of formula (9) ($R_4$=H) (0.92 grams). Yield: 80%.

$^1$H-NMR (CDCl$_3$): δ 3.65 (s, 2H), 3.0 (bs, 2H), 2.10-2.0 (m, 6H), 1.82 (bs, 2H), 1.65-1.57 (m, 4H);

Mass (m/z): 177 [M+H$^+$].

Step (ii): Preparation of Compound of Formula (10)

To a stirred solution of compound of formula (9) ($R_4$=H) (919 mg, 5.2 mmol) in dry tetrahydrofuran (10 mL) cooled to 0° C. was, added lithiumaluminium hydride (1M in tetrahydrofuran, 7.8 mL). The reaction was gradually warmed to room temperature and stirred for 30 minutes. The reaction was quenched by adding ice pieces and filtered through a small pad of celite. The filtrate was evaporated to dryness and purified by silica gel flash column chromatography to yield compound of formula (10) ($R_4$=H) (0.61 grams). Yield: 64%.

$^1$H-NMR (CDCl$_3$): δ 2.81 (bs, 2H), 2.78-2.65 (m, 4H), 2.12-1.92 (m, 6H), 1.81 (bs, 2H), 1.65-1.50 (m, 4H).

Mass (m/z): 181 [M+H$^+$].

Preparation 3

Preparation of Compound of Formula (23)

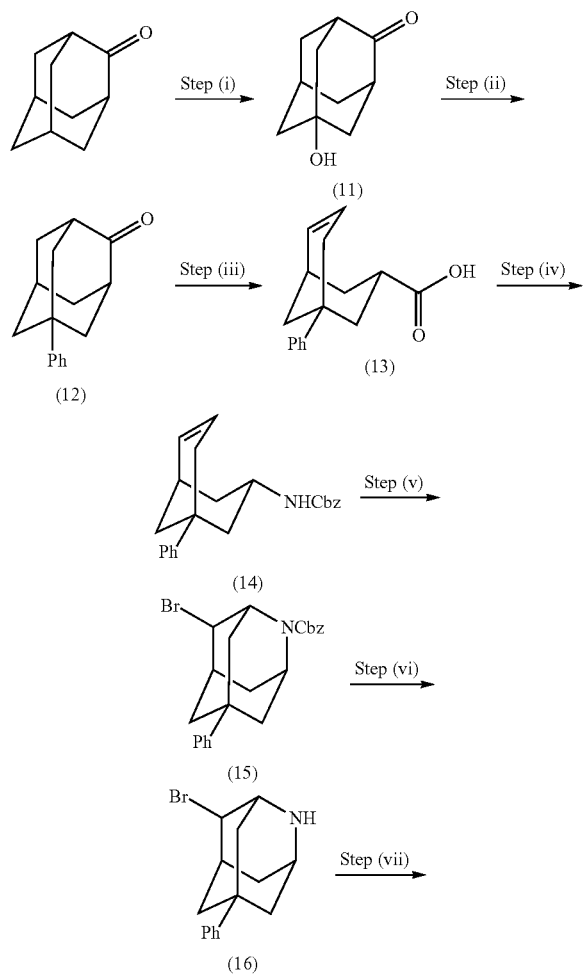

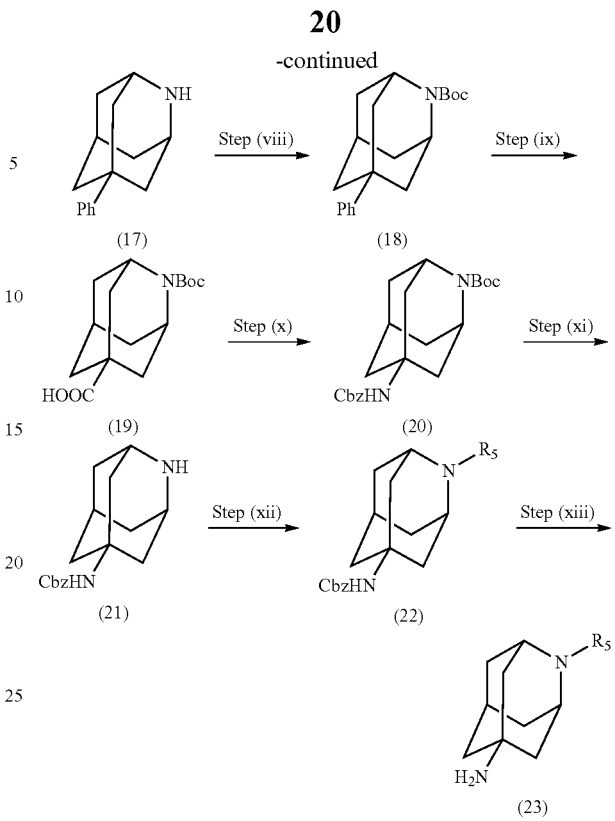

Step (i): Preparation of Compound of Formula (11)

Adamantanone (50 grams, 333 mmol) was added with stirring to nitric acid (98%, 440 mL) at ice bath temperature over a period of 15 minutes. The reaction mixture was stirred at room temperature for 72 hours and then heated at 60° C., for 2 hours until most of the nitrogen dioxide evaporated. Excess nitric acid was distilled off under reduced pressure. The light yellow oil solidified upon cooling. The reaction mixture was diluted with water (200 mL) and concentrated sulphuric acid (75 mL). The resultant clear yellow solution was heated on the steam bath in a hood for 1 hour. The reaction mixture was neutralized with 30% aqueous sodium-hydroxide solution, and while warm, extracted with chloroform. The extracts were combined, washed with brine solution and concentrated in vacuum. The crude product was dissolved in dichloromethane (15 mL) and hexane was added until no more precipitate was formed. The solid material was isolated by filtration and dried under vacuum to obtain compound of formula (11) (40.9 grams). Yield: 74%.

Melting Range: 278.8-300° C.;

$^1$H-NMR (CDCl$_3$): δ 2.69 (bs, 2H), 2.36-2.32 (m, 2H), 2.12-2.02 (m, 2H), 2.02-1.88 (m, 6H), 1.80-1.68 (m, 1H).

IR: 3410, 2929, 2855, 2645, 1725, 1539, 1452, 1351, 1288, 1116, 1055, 927, 900, 797;

Mass (m/z): 167 [M+H$^+$].

Step (ii): Preparation of Compound of Formula (12)

To a stirred solution of compound of formula (11) (20.0 grams, 120.3 mmol) in benzene (365 mL) was added trifluoromethanesulfonic acid (10.7 mL, 60.2 mmol) over a period of 40 minutes at room temperature. After stirring the reaction mixture for 5 minutes at room temperature it was refluxed for 4 hours. The reaction mixture was cooled to 0° C. and saturated aqueous sodium bicarbonate (150 mL) were added over a period of 30 minutes. Two layers were separated, the aqueous layer was extracted with ether and the combined organic layer was washed with water, brine, dried over anhydrous sodium sulphate and the solvent was evaporated under reduced pressure to obtain compound of formula (12) as a white solid (21.2 grams). Yield: 78%.

Melting Range: 53.8-60.9° C.;

$^1$H-NMR (CDCl$_3$): δ 7.37-7.22 (m, 4H), 7.17-7.10 (m, 1H), 2.67 (bs, 2H), 2.37-2.25 (m, 2H), 2.25-2.15 (m, 4H), 2.15-2.0 (m, 5H).

IR (cm$^{-1}$): 2912, 2850, 1716, 1597, 1495, 1444, 1294, 1059, 960, 758, 701.

Mass (m/z): 227 [M+H$^+$].

Step (iii): Preparation of Compound of Formula (13)

The compound of formula (13) is prepared by following same procedure as mentioned in step (i) of preparation 1, by using compound of formula (12).

$^1$H-NMR (CDCl$_3$): δ 7.50-7.30 (m, 4H), 7.27-7.15 (m, 1H), 5.80-5.70 (m, 1H), 5.70-5.60 (m, 1H), 2.90-2.56 (m, 4H), 2.55-2.10 (m, 3H), 2.10-2.0 (m, 1H), 2.0-1.67 (m, 2H).

IR (cm$^{-1}$): 3500, 3302, 2917, 1689, 1493, 1355, 1248, 947, 758, 699.

Mass (m/z): 243 [M+H$^+$].

Step (iv): Preparation of Compound of Formula (14)

The compound of formula (14) is prepared by following same procedure as mentioned in step (ii) of preparation 1, by using compound of formula (13).

$^1$H-NMR (CDCl$_3$): δ 7.45-7.25 (m, 8H), 7.25-7.17 (m, 2H), 6.18-5.70 (m, 2H), 5.20-5.12 (m, 2H), 5.10 (dd, J=24.1, 12.3 Hz, 1H), 4.20-4.10 (m, 1H), 3.20-3.0 (m, 2H), 2.90-2.81 (m, 1H), 2.27-2.10 (m, 1H), 2.10-2.0 (m, 1H), 1.97-1.70 (m, 4H).

IR (cm$^{-1}$): 3440, 3019, 1709, 1619, 1486, 1386, 1216, 1072, 957, 757.

Mass (m/z): 348 [M+H$^+$].

Step (v): Preparation of Compound of Formula (15)

The compound of formula (15) is prepared by following same procedure as mentioned in step (iii) of preparation 1, by using compound of formula (14).

$^1$H-NMR (CDCl$_3$): δ 7.45-7.30 (m, 8H), 7.30-7.18 (m, 2H), 5.23-5.13 (m, 2H), 4.70-4.36 (m, 3H), 2.70-2.44 (m, 3H), 2.15-1.70 (m, 6H).

IR (cm$^{-1}$): 3019, 2927, 1626, 1592, 1485, 1382, 1215, 1084, 956, 860, 757.

Mass (m/z): 426, 428 [M+H$^+$].

Step (vi): Preparation of Compound of Formula (16)

The compound of formula (16) as hydrochloride salt is prepared by following same procedure as mentioned in step (iv) of preparation 1, by using compound of formula (15).

$^1$H-NMR (CDCl$_3$): δ 9.81 (bs, 1H), 9.76 (bs, 1H), 7.44-7.30 (m, 4H), 7.30-7.25 (m, 1H), 4.96 (bs, 1H), 4.10-3.95 (m, 2H), 2.80-2.30 (m, 6H), 2.20-2.02 (m, 2H), 1.96-1.85 (m, 1H).

IR (cm$^{-1}$): 3438, 2922, 2787, 2470, 1582, 1494, 1431, 1381, 1348, 1109, 1004, 754, 701.

Mass (m/z): 292, 294 [M+H$^+$].

Step (vii): Preparation of Compound of Formula (17)

The compound of formula (17) is prepared by following same procedure as mentioned in step (v) of preparation 1, by using compound of formula (16).

$^1$H-NMR (CDCl$_3$): δ 7.40-7.30 (m, 4H), 7.25-7.20 (m, 1H), 3.80-3.70 (m, 3H), 2.48-2.25 (m, 5H), 2.10-1.95 (m, 4H), 1.90-1.80 (m, 2H).

IR (cm$^{-1}$): 3422, 3153, 2915, 2846, 1599, 1492, 1443, 1105, 1022, 756, 698.

Mass (m/z): 214 [M+H$^+$].

Step (viii): Preparation of Compound of Formula (18)

To a stirred solution of compound of formula (17) (1.3 grams, 6.1 mmol) in dichloromethane (20 mL) cooled at 0° C. was added triethylamine (1.1 mL, 7.9 mmol) and Boc anhydride (1.46 grams, 6.7 mmol). The reaction mixture was gradually warmed to room temperature and stirred for 16 hours. The volatiles were removed under reduced pressure and the crude mass was purified by silica gel flash column chromatography to obtain compound of formula (18) (1.3 grams). Yield: 68%.

$^1$H-NMR (CDCl$_3$): δ 7.40-7.30 (m, 4H), 7.24-7.18 (m, 1H), 4.55-4.48 (m, 1H), 4.42-4.35 (m, 1H), 2.30-2.24 (m, 1H), 2.05-1.83 (m, 7H), 1.78-1.64 (m, 3H), 1.48 (s, 9H).

IR (cm$^{-1}$): 2984, 2926, 2855, 1687, 1447, 1403, 1361, 1167, 1100, 1077, 753, 702.

Mass (m/z): 314 [M+H$^+$].

Step (ix): Preparation of Compound of Formula (19)

To a stirred mixture of compound of formula (18) (2.0 grams, 6.3 mmol), carbontetrachloride (16 mL), acetonitrile (16 mL) and water (25 mL) cooled at 0° C., was added sodiumperiodate (5.98 grams, 28 mmol) and ruthenium (III) chloride hydrate (0.08 grams, 0.4 mmol). The reaction mixture was gradually warmed to room temperature and after stirring for 3 hours, diluted with isopropylether (100 mL) and stirred for 15 minutes to precipitate black RuO$_2$. The reaction mixture is then filtered through a pad of celite and the layers were separated. The organic layer was washed with 1N sodium hydroxide solution. The organic layer was dried over sodium sulphate and the solvent was evaporated under reduced pressure to obtain unreacted starting material (1.4 grams). The combined aqueous layer was acidified with concentrated hydrochloric acid and extracted with ethylacetate. The combined organic layer was washed with brine, dried over sodium sulphate and the solvent was removed under reduced pressure to obtain compound of formula (19) (0.6 grams). Yield: 33%.

$^1$H-NMR (CDCl$_3$): δ 4.45-4.40 (m, 1H), 4.35-4.28 (m, 1H), 2.22-2.18 (m, 1H), 2.08-1.76 (m, 7H), 1.78-1.60 (m, 3H), 1.46 (s, 9H).

IR (cm$^{-1}$): 3472, 3367, 3018, 2932, 1702, 1678, 1418, 1365, 1216, 1170, 1116, 1103, 758, 668.

Mass (m/z): 280 [M−H$^+$].

Step (x): Preparation of Compound of Formula (20)

The compound of formula (20) is prepared by following same procedure as mentioned in step (ii) of preparation 1, by using compound of formula (19).

$^1$H-NMR (CDCl$_3$): δ 7.42-7.30 (m, 4H), 7.30-7.20 (m, 1H), 5.04 (s, 2H), 4.70 (bs, 1H), 4.50-4.42 (m, 1H), 4.38-4.32 (m, 1H), 2.30-2.20 (m, 1H), 2.18-1.87 (m, 5H), 1.85-1.52 (m, 5H), 1.46 (s, 9H).

IR (cm$^{-1}$): 3406, 3019, 2931, 1592, 1579, 1485, 1389, 1215, 1049, 955, 861, 757, 669.

Mass (m/z): 387 [M+H$^+$].

Step (xi): Preparation of Compound of Formula (21)

To a stirred solution of compound of formula (20) (0.497 grams, 1.28 mmol) in dichloromethane (10 mL) cooled at 0° C. was added trifluoroacetic acid (1.28 mL). The reaction mixture was gradually warmed to room temperature and stirred for 2 hours. The volatiles were removed under reduced pressure, the residue was diluted with 10% aqueous sodium bicarbonate and extracted with dichloromethane to afford compound of formula (21) (0.35 grams). Yield: 97%.

$^1$H-NMR (CDCl$_3$): δ 7.42-7.20 (m, 5H), 5.10-5.0 (s, 2H), 4.75 (bs, 1H), 3.80-3.68 (m, 2H), 2.35-2.30 (m, 1H), 2.30-2.10 (m, 8H), 1.80-1.70 (m, 2H).

IR (cm$^{-1}$): 3431, 3019, 2956, 2868, 1664, 1629, 1593, 1485, 1388, 1288, 1216, 1056, 757, 668.

Mass (m/z): 287 [M+H$^+$].

Step (xii): Preparation of Compound of Formula (22)

To the compound of formula (21) (170 mg, 0.59 mmol) were added formic acid (2 mL) and formaldehyde (4 mL), and the reaction mixture was stirred at 80° C. for 4 hours. The reaction was quenched with water and saturated potassium carbonate and the mixture was extracted with dichloromethane. The extract was dried over sodium sulphate and reduced in volume, and the residue was purified by flash chromatography on silica gel to obtain compound of formula (22) ($R_5$=Methyl) (200 mg). Yield: Quantitative $^1$H-NMR (CDCl$_3$): δ 7.40-7.20 (m, 5H), 5.05 (s, 2H), 4.65 (bs, 1H), 3.08-2.97 (m, 2H), 2.53 (s, 3H), 2.32-2.20 (m, 2H), 2.20-2.14 (m, 1H), 2.06-1.95 (m, 3H), 1.70-1.50 (m, 5H).

IR (cm$^{-1}$): 3432, 3019, 2929, 2857, 1719, 1592, 1487, 1379, 1284, 1216, 1049, 757, 668.

Mass (m/z): 301 [M+H$^+$].

Step (xiii): Preparation of Compound of Formula (23)

To a stirred solution of compound of formula (22) ($R_5$=Methyl) (0.4 grams, 1.3 mmol) in methanol (1.6 mL), under nitrogen atmosphere was added Pd/C (10%, 0.20 grams). The double-layered balloon filled with hydrogen gas was applied. After stirring for 16 hours at room temperature the reaction mixture was filtered through a small pad of celite and the filtrate evaporated under reduced pressure to obtain compound of formula (23) ($R_5$=Methyl) (0.2 grams). Yield: 90%.

$^1$H-NMR (CDCl$_3$): δ 3.10-3.0 (m, 2H), 2.52 (s, 3H), 2.20-2.10 (m, 1H), 2.10-1.84 (m, 5H), 1.70-1.60 (m, 2H), 1.50-1.35 (m, 3H).

IR (cm$^{-1}$): 3413, 3019, 2928, 2854, 1627, 1581, 1486, 1383, 1216, 1084, 954, 757, 668.

Mass (m/z): 167 [M+H$^+$].

Preparation 4

Preparation of Compound of Formula (27)

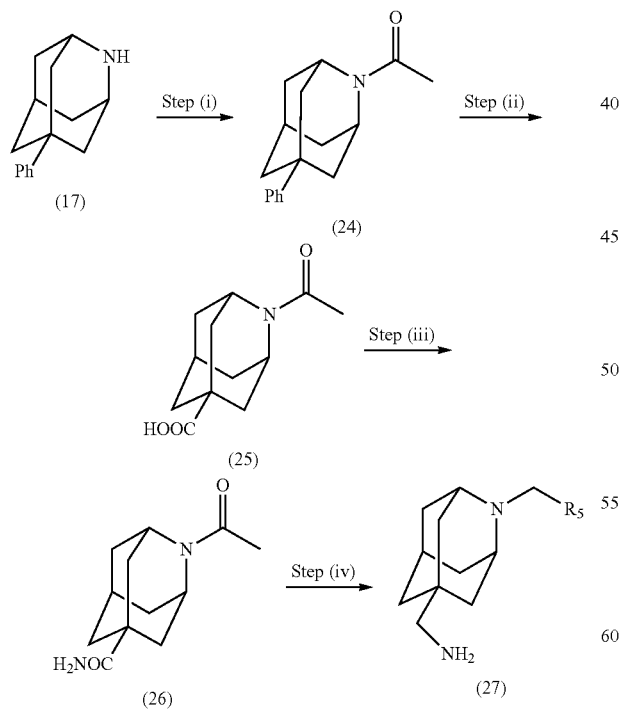

Step (i): Preparation of Compound of Formula (24)

To a stirred solution of compound of formula (17) (2.5 grams, 11.73 mmol) in dichloromethane (47 mL) cooled at 0° C. was added triethylamine (2.45 mL, 17.6 mmol), 4-dimethylaminopyridine (122 mg. 1.0 mmol) and acetic anhydride (1.56 mL, 15.2 mmol). The reaction mixture was gradually warmed to room temperature and stirred for 2 hours. The volatiles were removed under reduced pressure and the crude product dissolved in water and extracted with ethylacetate. The combined organic layer dried over anhydrous sodium sulphate and the solvent was removed to obtain compound of formula (24) (3.0 grams). Yield: 100%.

$^1$H-NMR (CDCl$_3$): δ 7.40-7.30 (m, 4H), 7.25-7.15 (m, 1H), 5.10-4.95 (m, 1H), 4.25-4.18 (m, 1H), 2.35-2.25 (m, 1H), 2.12 (s, 3H), 2.05-1.55 (m, 10H).

Mass (m/z): 256 [M+H$^+$].

Step (ii): Preparation of Compound of Formula (25)

The compound of formula (25) is prepared by following same procedure as mentioned in step (ix) of preparation 3, by using compound of formula (24).

$^1$H-NMR (DMSO-d$_6$): δ 4.70-4.63 (m, 1H), 4.10-4.02 (m, 1H), 2.15-2.05 (m, 1H), 1.94 (s, 3H), 1.90-1.75 (m, 5H), 1.75-1.55 (m, 5H).

Mass (m/z): 224 [M+H$^+$].

Step (iii): Preparation of Compound of Formula (26)

To a stirred solution of compound of formula (25) (400 mg, 1.79 mmol) in acetonitrile (7 mL) at room temperature was added pyridine (0.16 mL, 1.97 mmol), Boc anhydride (470 mg, 2.15 mmol). After 1 hour solid ammonium bicarbonate (230 mg, 2.9 mmol) was added and the reaction mixture was stirred for 12 hours. The volatiles were removed under vacuum to and the crude product was purified by silica gel column chromatography to obtain compound of formula (26) (250 mg). Yield: 63%.

$^1$H-NMR (DMSO-d$_6$): δ 7.03 (bs, 1H), 6.79 (bs, 1H), 4.72-4.67 (m, 1H), 4.12-4.06 (m, 1H), 2.15-2.08 (m, 1H), 1.94 (s, 3H), 1.90-1.55 (m, 10H).

Mass (m/z): 223 [M+H$^+$].

Step (iv): Preparation of Compound of Formula (27)

To a stirred solution of compound of formula (26) (240 mg, 1.08 mmol) in dry tetrahydrofuran cooled at 0° C. was added a 1M solution of lithium aluminum hydride in tetrahydrofuran (3.5 mL, 3.5 mmol). The reaction mixture was gradually warmed to room temperature then refluxed for 6 hours. The reaction mixture was cooled to 0° C., ice pieces were added carefully and stirred for 30 minutes before filtered through a small pad of celite. The filtrate was evaporated and the crude product was purified by silica gel flash column chromatography to obtain compound of formula (27) ($R_5$=Methyl) (160 mg). Yield: 76%.

$^1$H-NMR (CDCl$_3$): δ 3.10-3.0 (m, 2H), 2.80-2.70 (q, 2H), 2.36 (s, 2H), 2.20-1.20 (m, 9H), 1.11 (t, 3H), 0.90-0.75 (m, 2H).

Mass (m/z): 195 [M+H$^+$].

Preparation 5

Preparation of Compound of Formula (32)

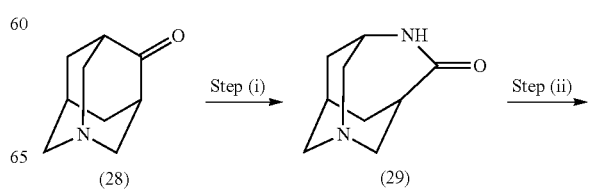

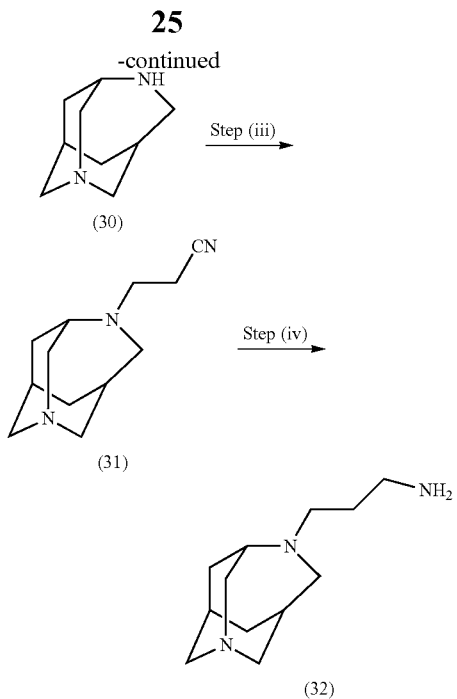

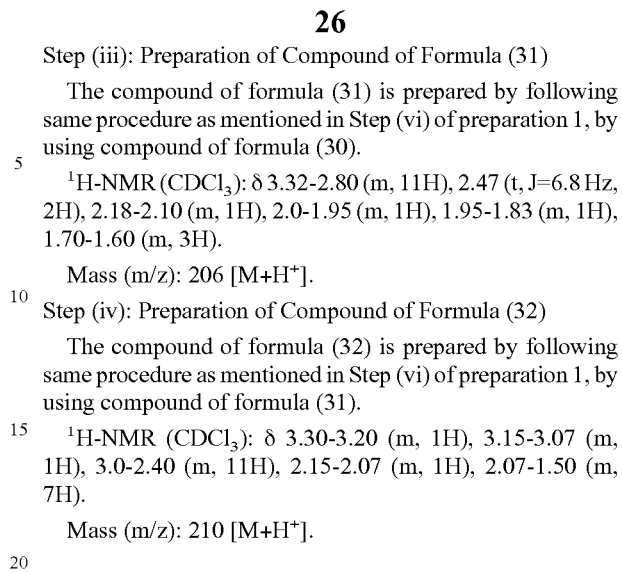

Step (i): Preparation of Compound of Formula (29)

To a stirred solution of compound of formula (28) (2.0 grams, 13.2 mmol) in methanesulfonic acid (12.5 grams) was added sodium azide (0.9 grams, 3.98 mmol) portion wise over 2 hours. The temperature was maintained at 20-25° C. during the addition. Nitrogen evolution ceased 2 hours after the addition was completed. After stirring an additional hour at room temperature, the reaction solution was diluted with 100 mL of water. An excess of 50% potassium hydroxide solution was carefully added portion wise without external cooling. The exothermic reaction yielded a solution, which was extracted with ethylacetate. The combined organic layer was washed with brine, dried over anhydrous sodium sulphate and the solvent was removed under reduced pressure to obtain a crude mass which was purified by silica gel flash column chromatography to obtain compound of formula (29) (1.56 grams). Yield: 71%.

$^1$H-NMR (CD$_3$OD): δ 3.30-3.15 (m, 7H), 2.48-2.40 (m, 1H), 2.25-2.10 (m, 2H), 2.10-2.02 (m, 1H), 2.0-1.92 (m, 1H), 1.88-1.82 (m, 1H).

Mass (m/z): 167 [M+H$^+$].

Step (ii): Preparation of Compound of Formula (30)

To a stirred solution of compound of formula (29) (1.5 grams, 9.0 mmol) in dry tetrahydrofuran (36 mL) was added borane in tetrahydrofuran (1M, 18 mL). The reaction mixture was refluxed for 16 hours. The reaction mixture was cooled to 0° C. and quenched by adding a 1N hydrochloric acid solution. Layers were separated and the aqueous layer was washed with ethylacetate then basified with 50% sodium hydroxide solution and extracted with 1:9 methanol:chloroform system. The combined organic layer was dried over anhydrous sodium sulphate and the crude product was purified by silica gel flash chromatography to obtain compound of formula (30) (1.16 grams). Yield: 85%.

$^1$H-NMR (CDCl$_3$): δ 3.30-3.03 (m, 5H), 2.90-2.75 (m, 4H), 2.18-2.08 (m, 2H), 2.05-1.88 (m, 2H), 1.68-1.58 (m, 2H).

Mass (m/z): 153 [M+H$^+$].

Step (iii): Preparation of Compound of Formula (31)

The compound of formula (31) is prepared by following same procedure as mentioned in Step (vi) of preparation 1, by using compound of formula (30).

$^1$H-NMR (CDCl$_3$): δ 3.32-2.80 (m, 11H), 2.47 (t, J=6.8 Hz, 2H), 2.18-2.10 (m, 1H), 2.0-1.95 (m, 1H), 1.95-1.83 (m, 1H), 1.70-1.60 (m, 3H).

Mass (m/z): 206 [M+H$^+$].

Step (iv): Preparation of Compound of Formula (32)

The compound of formula (32) is prepared by following same procedure as mentioned in Step (vi) of preparation 1, by using compound of formula (31).

$^1$H-NMR (CDCl$_3$): δ 3.30-3.20 (m, 1H), 3.15-3.07 (m, 1H), 3.0-2.40 (m, 11H), 2.15-2.07 (m, 1H), 2.07-1.50 (m, 7H).

Mass (m/z): 210 [M+H$^+$].

Preparation 6

Preparation of Compound of Formula (41)

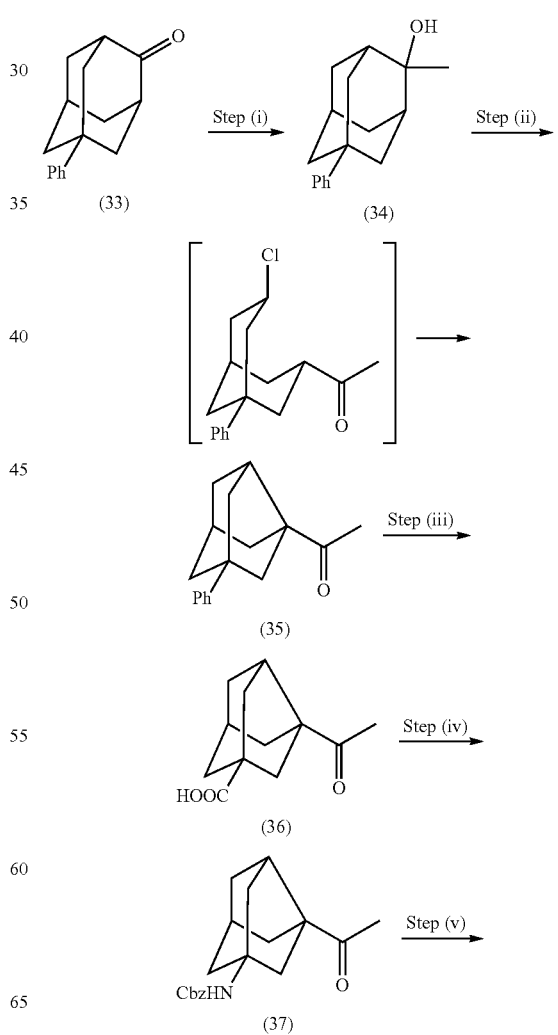

-continued

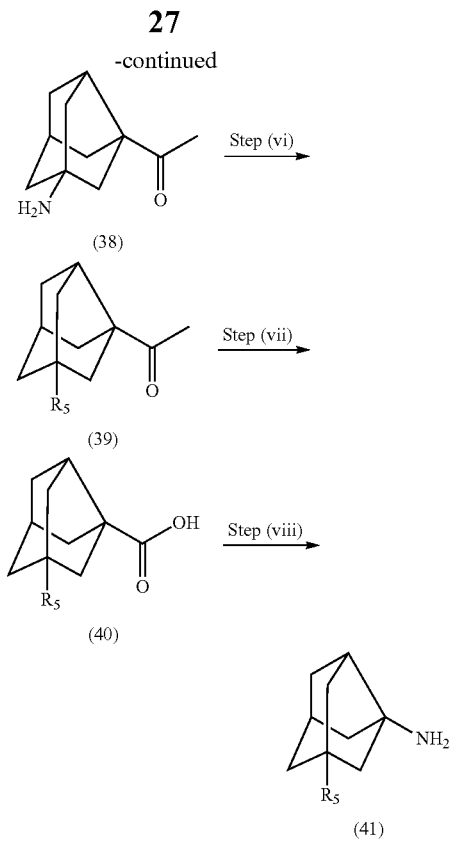

Step (i): Preparation of Compound of Formula (34)

Freshly prepared methyl magnesium iodide in ether (1M, 253 mL), was added through canola to compound of formula (33) (22 grams, 93.3 mmol) in tetrahydrofuran (195 mL) at 0° C. After stirring at 0° C. for 0.5 hour, the reaction mixture was quenched by adding saturated aqueous ammonium chloride solution. The organic layer was separated and the aqueous layer was extracted with diethylether. The combined organic layer was washed with water, brine, dried over anhydrous sodium sulphate and the solvent was removed under reduced pressure to obtain compound of formula (34) as off-white solid (22.4 grams). Yield: 95%.

Melting Range: 98-100.4° C.;

$^1$H-NMR (CDCl$_3$): δ 7.42-7.28 (m, 4H), 7.24-7.18 (m, 1H), 2.47-2.42 (m, 1H), 2.32-2.25 (m, 1H), 2.14-2.01 (m, 3H), 1.96-1.85 (m, 5H), 1.80-1.67 (m, 2H), 1.60-1.54 (m, 2H), 154-1.45 (m, 1H), 1.41 (s, 3H).

Mass (m/z): 243 [M+H$^+$].

Step (ii): Preparation of Compound of Formula (35)

To compound of formula (34) (6.6 grams, 27.3 mmol) dissolved in a mixture of acetic acid (5.8 mL) and tetrahydrofuran (29 mL) was added drop wise through addition funnel to the ice bath cooled sodiumhypochloride (4%, 272 mL) solution over a period of 15 minutes. Solid tetrabutylammonium iodide (1.0 grams, 2.7 mmol) was added and the reaction mixture was stirred for 1.5 hours. The two layers were separated, the aqueous layer was extracted with diisopropylether and the combined organic layer was washed with water, brine, dried over sodium sulphate and the solvent was removed under reduced pressure. The residue was dissolved in methanol (14 mL), solid potassium hydroxide (3.0 grams, 54.6 mmol) was added and the mixture was refluxed for 1 hour. The solvent was evaporated under reduced pressure and the crude product was purified by column chromatography to yield compound of formula (35) (2.85 grams) as viscous liquid. Yield: 44%

$^1$H-NMR (CDCl$_3$) δ 7.38-7.26 (m, 4H), 7.24-7.17 (m, 1H), 2.86-2.80 (m, 1H), 2.59-2.50 (m, 1H), 2.30-2.20 (m, 1H), 2.22 (s, 3H), 2.10-1.92 (m, 4H), 1.92-1.75 (m, 4H), 1.82-1.70 (m, 1H).

IR (cm$^{-1}$): 2924, 2867, 1697, 1445, 1356, 1223, 757, 699;

Mass (m/z): 241 [M+H$^+$].

Step (iii): Preparation of Compound of Formula (36)

To a stirred mixture of compound of formula (35) (2.8 grams, 11.66 mmol) as obtained in preparation 1, carbon tetrachloride (24 mL), acetonitrile (24 mL) and water (36 mL) cooled at 0° C., was added sodiumperiodate (11.2 grams, 52.2 mmol) followed by ruthenium (III) chloride hydrate (0.13 grams, 0.6 mmol). The reaction mixture was gradually warmed to room temperature and stirred for 2 hours. The reaction mixture was diluted with isopropylether (100 mL) and stirred for 15 minutes to precipitate black RuO$_2$. The reaction mixture is then filtered through a pad of celite and the organic layer was extracted with 1N sodium hydroxide solution (3×25 mL). The organic layer was dried over sodium sulphate; solvent was evaporated under vacuum to obtain unreacted starting material (1.32 grams, 5.5 mmol). The aqueous layer was acidified with concentrated hydrochloric acid and extracted in ethylacetate. The combined organic layer was washed with brine, dried over sodium sulphate and the solvent was removed under reduced pressure to obtain compound of formula (36) (0.9 gram) as off-white solid. Yield: 35%.

Melting Range: 90-95.0° C.;

$^1$H-NMR (CDCl$_3$) 2.80-2.72 (m, 1H), 2.56-2.50 (m, 1H), 2.44-2.37 (m, 1H), 2.20 (s, 3H), 2.18-2.09 (m, 1H), 2.02-1.85 (m, 4H), 1.85-1.72 (m, 3H), 1.68-1.62 (m, 1H).

IR (cm$^{-1}$): 2935, 1694, 1413, 1357, 974, 746.

Mass (m/z): 207 [M−H$^+$].

Step (iv): Preparation of Compound of Formula (37)

The compound of formula (37) is prepared by following same procedure as mentioned in Step (x) of preparation 3, by using compound of formula (36).

$^1$H-NMR (CDCl$_3$): δ 7.40-7.27 (m, 5H), 5.05 (s, 2H), 4.95 (bs, 1H), 2.75-2.65 (m, 1H), 2.47 (bs, 1H), 2.50-2.42 (m, 1H), 2.28-2.15 (m, 1H), 2.17 (s, 3H), 2.10-1.82 (m, 4H), 1.80-1.70 (m, 2H), 1.70-1.53 (m, 2H).

Mass (m/z): 314 [M+H$^+$].

Step (v): Preparation of Compound of Formula (38)

The compound of formula (38) is prepared by following same procedure as mentioned in Step (xiii) of preparation 3, by using compound of formula (37).

$^1$H-NMR (CDCl$_3$): δ 2.72-2.65 (m, 1H), 2.52-2.47 (m, 1H), 2.17 (s, 3H), 2.15-2.08 (m, 1H), 1.98-1.86 (m, 2H), 1.80-1.50 (m, 7H).

Mass (m/z): 180 [M+H$^+$].

Step (vi): Preparation of Compound of Formula (39)

To a solution of compound of formula (38) (173 mg, 1.0 mmol) in dimethyl formamide (2.5 mL), anhydrous triethylamine (0.4 mL, 2.9 mmol) was added and the suspension was stirred at room temperature for 2 hours. 1,4-Dibromobutane (0.17 mL, 1.2 mmol) was added and the mixture was heated at 60° C. for 26 hours. To the cold mixture, water (15 mL) was added and the solution was washed with ethylacetate. The aqueous phase was basified with 2 N sodium hydroxide and extracted with ethyl acetate. The combined organic extracts were washed with water, dried with anhydrous sodium sulphate, filtered and the solvent was removed in vacuum to dryness to give compound of formula (39) (R$_5$=Pyrrolidin-1-yl) (117 mg). Yield: 52%.

$^1$H-NMR (CDCl$_3$): δ 2.80-2.68 (m, 4H), 2.68-2.63 (m, 1H), 2.53-2.48 (m, 1H), 2.24-2.19 (m, 1H), 2.18 (s, 3H), 2.0-1.90 (m, 2H), 1.90-1.50 (m, 11H);

Mass (m/z): 234 [M+H$^+$].

Step (vii): Preparation of Compound of Formula (40)

To a stirred solution of sodium hydroxide (6.3 gams, 158.0 mmol), water (54.0 mL) and 1,4 dioxan (7 mL) at 0° C. was added bromine (3.2 mL, 59.0 mmol) and stirred for 5 minutes. Thus formed hypobromite solution was added dropwise to a stirred solution of compound of formula (39) (R$_5$=Pyrrolidin-1-yl) (3.0 grams, 10.53 mmol) in 1,4-dioxan (14 mL) at ice bath temperature. The reaction mixture was gradually warmed to room temperature and stirred for 1 hour. The reaction mixture was cooled to 0° C., acidified (pH 2-3) with 5N hydrochloric acid and washed with ethylacetate. The aqueous layer was evaporated to dryness and the crude product was purified by silica gel flash chromatography to obtain compound of formula (40) (R$_5$=Pyrrolidin-1-yl) (2.27 grams). Yield: 75%.

$^1$H-NMR (CDCl$_3$): δ 11.69 (bs, 1H), 3.70-3.56 (m, 2H), 3.05-2.92 (m, 2H), 2.90-2.83 (m, 1H), 2.66-2.58 (m, 1H), 2.40-2.20 (m, 3H), 2.18-1.60 (m, 11H).

Mass (m/z): 236 [M+H$^+$].

Step (viii): Preparation of Compound of Formula (41)

To the stirred solution of compound of formula (40) (R$_5$=Pyrrolidin-1-yl) (3.0 grams, 10.45 mmol) chloroform (21 mL) was added concentrated sulphuric acid (4.2 mL, 78.9 mmol) then solid sodiumazide (2.38 g, 36.6 mmol) was added in portions, so that the temperature of the reaction does not rise above 40° C. After the addition was completed, the reaction mixture was warmed to 45° C. and stirred for 2 hours. The reaction mixture was cooled to 0° C., diluted with water and extracted with ethylacetate. The aqueous layer was basified with 50% sodium hydroxide solution and extracted with chloroform. The combined organic layer was washed with brine, dried over sodium hydroxide and solvent was removed under reduced pressure to obtain compound of formula (41) (R$_5$=Pyrrolidin-1-yl) as off-white solid (2.0 grams). Yield: 76%.

$^1$H-NMR (CDCl$_3$): δ 2.80-2.60 (m, 4H), 2.40-2.33 (m, 1H), 2.15-2.06 (m, 1H), 2.0-1.92 (m, 1H), 1.90-1.40 (m, 13H).

Mass (m/z): 207 [M+H$^+$].

Preparation 7

Preparation of Compound of Formula (43)

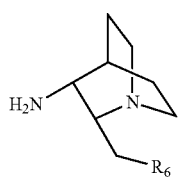

(43)

To a stirred solution of 2-[(2-pyridinyl)methyl]-1-azabicyclo[2.2.2]octan-3-one (42) (1 gram, 4.6 mmol, 1 equivalent) in dry methanol (6.6 mL), under nitrogen, was added a 1 M solution of zincchloride in ether (0.9 mL, 0.9 mmol, 0.2 equivalent). After stirring at ambient temperature for 30 minutes, this mixture was treated with solid ammonium formate (3.48 grams, 55.37 mmol, 11.96 equivalents). After stirring another hour at ambient temperature, solid sodium cyanoborohydride (0.581 grams, 9.2 mmol, 2 equivalents) was added in portions. The reaction was then stirred at ambient temperature overnight and terminated by addition of water (5 mL). The quenched reaction was partitioned between 5 M sodium hydroxide (10 mL) and chloroform (20 mL). The aqueous layer was extracted with chloroform (20 mL), and combined organic layers were dried sodium sulphate, filtered and concentrated. This left 2.97 grams of yellow gum product (43, R$_6$=2-Pyridinyl). GC-MS analysis indicated that the product was a 90:10 mixture of the cis and trans amines, along with a trace of the corresponding alcohol. Yield: 98%.

$^1$H-NMR (CDCl$_3$): δ 8.55 (d, J=5.0 Hz, 1H), 7.61 (t, J=7.6 Hz, 1H), 7.25 (d, J=7.9 Hz, 1H), 7.13 (dd, J=7.3, 5.0 Hz, 1H), 3.15-2.70 (m, 8H), 2.0-1.30 (m, 5H);

Mass (m/z): 218 [M+H$^+$].

Preparation 8

Preparation of Compound of Formula (46)

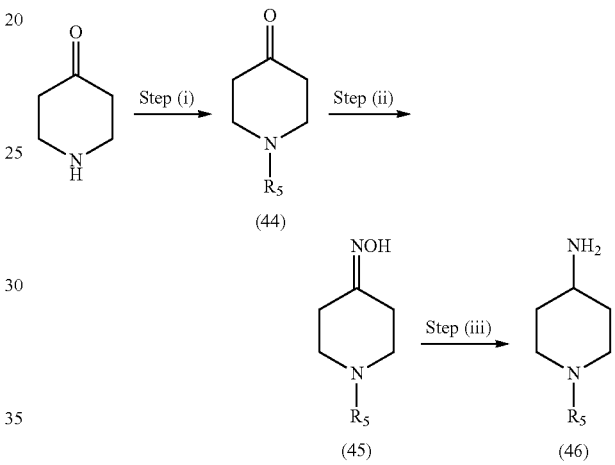

Step (i): Preparation of Compound of Formula (44)

To a stirred solution of hydrochloride salt of piperidin-4-one (3.6 grams, 26.5 mmol) in acetonitrile (106 mL) was added cesium carbonate (25.9 grams, 79.7 mmol). After stirring for 30 minutes, chlorobutane (4.16 mL, 39.85 mmol) followed by sodium iodide (11.96 grams, 79.7 mmol). The reaction mixture was refluxed for 2 hours and filtered through pad of celite. The filtrate was evaporated to dryness under reduced pressure and the crude product was purified by silica gel column chromatography to obtain compound of formula (44) (R$_5$=n-butyl) (2.92 grams). Yield: 71%.

$^1$H-NMR (CDCl$_3$): δ 2.85-2.70 (m, 4H), 2.55-2.40 (m, 6H), 1.60-1.50 (m, 2H), 1.45-1.30 (m, 2H), 0.94 (t, J=7.2 Hz, 3H).

Mass (m/z): 156 [M+H$^+$].

Step (ii): Preparation of Compound of Formula (45)

To a solution of compound of formula (44) (R$_5$=n-butyl) (2.9 grams, 18.7 mmol) pyridine (2.5 mL, 32.1 mmol) in ethanol (85 mL) was added hydroxylamine hydrochloride (2.23 grams, 32.1 mmol) and refluxed for 2 hours. The volatiles were removed under reduced pressure; the crude product was dissolved in water and extracted with 10% methanolic ammonia in chloroform. The combined organic layer was dried over anhydrous Na$_2$SO$_4$ and the solvent was evaporated under reduced pressure to obtain oxime compound of formula (45) (R$_5$=n-butyl) (2.0 grams). Yield: 63.0%.

$^1$H-NMR (CDCl$_3$): δ 7.22 (bs, 1H), 2.80-2.55 (m, 6H), 2.50-2.35 (m, 4H), 1.60-1.50 (m, 2H), 1.40-1.30 (m, 2H), 0.93 (t, J=7.2 Hz, 3H).

Mass (m/z): 171 [M+H$^+$].

Step (iii): Preparation of Compound of Formula (46)

To a stirred solution of compound of formula (45) ($R_5$=n-butyl) (1.6 grams, 9.39 mmol) in n-propanol (37 mL) was added in portions sodium metal (2.3 grams, 100 mmol). The reaction mixture was refluxed for 1 hour. The reaction mixture was diluted with n-propanol, water and stirred for 30 minutes. The volatiles were removed under reduced pressure and the crude product was purified by silica gel flash chromatography to obtain amine compound of formula (45) ($R_5$=n-butyl) (1.0 grams). Yield: 68%.

$^1$H-NMR (CDCl$_3$): δ 2.95-2.83 (m, 2H), 2.73-2.60 (m, 1H), 2.40-2.27 (m, 2H), 2.10-1.93 (m, 2H), 1.90-1.80 (m, 2H), 1.55-1.25 (m, 6H), 0.91 (t, J=7.3 Hz, 3H).

Mass (m/z): 157 [M+H$^+$].

Preparation 9

Preparation of Compound of Formula (53)

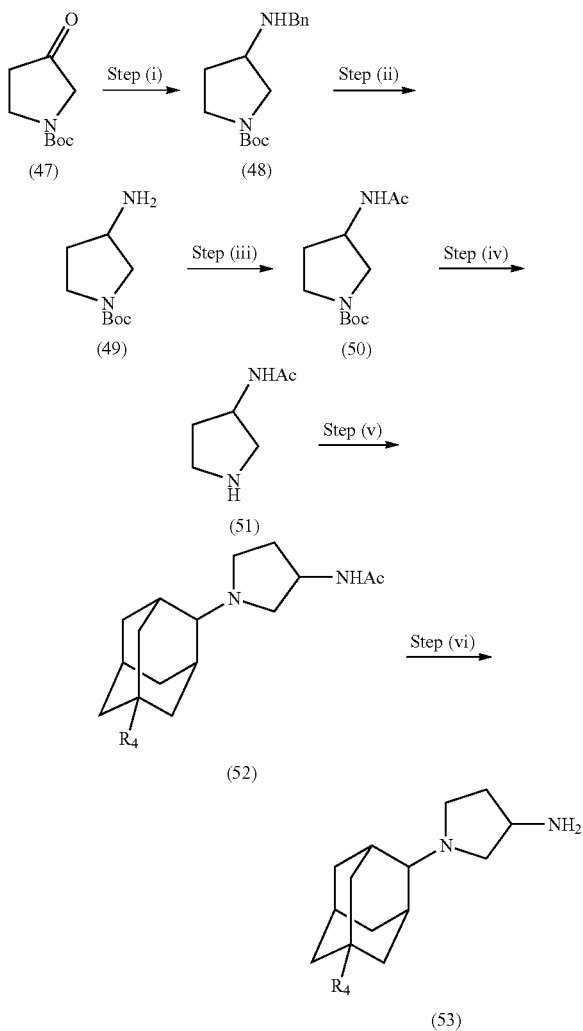

Step (i): Preparation of Compound of Formula (48)

To a stirred solution of compound of formula (47) (1.0 gram, 5.44 mmol) in dichloromethane (22 mL) cooled at 0° C. was added benzylamine (0.62 mL, 5.72 mmol), acetic acid (0.3 mL, 5.44 mmol) followed by sodium triacetoxy borohydride (1.8 grams, 8.51 mmol). The reaction was gradually warmed to room temperature and stirred for 7 hours. The reaction was quenched by adding aqueous sodium bicarbonate solution after cooling the reaction to 0° C. The two layers were separated, the aqueous layer extracted with dichloromethane, combined organic layer was washed with brine, dried over anhydrous sodium sulphate and the solvent was removed under reduced pressure. The crude product, thus obtained, was purified by silica gel flash column chromatography to obtain compound of formula (48) (1.18 grams). Yield: 79%.

$^1$H-NMR (CDCl$_3$): δ 7.40-7.20 (m, 5H), 3.81 (s, 2H), 3.65-3.42 (m, 2H), 3.42-3.28 (m, 2H), 3.25-3.08 (m, 1H), 2.12-2.02 (m, 1H), 1.83-1.70 (m, 1H), 1.46 (s, 9H).

Mass (m/z): 277 [M+H$^+$].

Step (ii): Preparation of Compound of Formula (49)

To a stirred solution of compound of formula (48) (1.15 grams, 4.16 mmol) in methanol (16.6 mL) was added 10% Pd/C (345 mg). Hydrogen pressure was applied through a double-layered balloon and the reaction was stirred for 16 hours. The reaction was filtered through a small pad of celite and the filtrate was removed under reduced pressure. The crude product was purified by silica gel flash column chromatography to obtain compound of formula (49) (640 mg). Yield: 82%.

$^1$H-NMR (CDCl$_3$): δ 3.65-3.45 (m, 3H), 3.45-3.33 (m, 1H), 3.20-3.0 (m, 1H), 2.12-2.02 (m, 1H), 1.80-1.65 (m, 1H), 1.46 (s, 9H).

Mass (m/z): 187 [M+H$^+$].

Step (iii): Preparation of Compound of Formula (50)

To a stirred solution of compound of formula (49) (620 mg, 3.33 mmol) in dichloromethane (13 mL) cooled at 0° C. was added triethylamine (0.69 mL, 5.0 mmol), 4-dimethylaminopyridine (6.5 mg, 0.5 mmol) and acetic anhydride (0.35 mL, 3.66 mmol). After stirring the reaction for 1 hour, the reaction was diluted with dichloromethane, washed with water, brine, dried over anhydrous sodium sulphate and the solvent was removed under reduced pressure to obtain compound of formula (50) (759 mg). Yield: 100%.

$^1$H-NMR (CDCl$_3$): δ 5.54 (bs, 1H), 4.52-4.42 (m, 1H), 3.61 (dd, J=11.4, 6.1 Hz, 1H), 3.42 (t, J=7.4 Hz, 2H), 3.18 (dd, J=11.4, 3.8 Hz, 1H), 2.22-2.10 (m, 1H), 1.99 (s, 3H), 1.90-1.80 (m, 1H), 1.47 (s, 9H).

Mass (m/z): 229 [M+H$^+$].

Step (iv): Preparation of Compound of Formula (51)

To the compound of formula (50) cooled at 0° C. was added a solution of dry hydrochloride in isopropanol (3M, 5 mL). The reaction was stirred at room temperature for 1 hour; the volatiles were removed under reduced pressure. The crude product was triturated with hexane followed by ether to obtain compound of formula (51) as hydrochloride salt (506 mg). Yield: 93%.

$^1$H-NMR (DMSO-d$_6$): δ 9.39 (bs, 1H), 9.34 (bs, 1H), 8.34 (bs, 1H), 4.28-4.18 (m, 1H), 3.33-3.22 (m, 2H), 3.22-3.12 (m, 1H), 3.0-2.88 (m, 1H), 2.10-2.0 (m, 1H), 1.85-1.72 (m, 1H), 1.80 (s, 3H).

Mass (m/z): 129 [M+H$^+$].

Step (v): Preparation of Compound of Formula (52)

The compound of formula (52) ($R_4$=H) is prepared by following same procedure as mentioned in Step (i) of preparation 9, by using compound of formula (51). Yield: 52%.

$^1$H-NMR (CDCl$_3$): δ 5.81 (bs, 1H), 4.55-4.40 (m, 1H), 3.0-2.80 (m, 1H), 2.75-2.60 (m, 1H), 2.50-2.35 (m, 1H), 2.30-2.0 (m, 5H), 1.98 (s, 3H), 2.0-1.75 (m, 6H), 1.75-1.60 (m, 5H), 1.50-1.40 (m, 2H).

Mass (m/z): 263 [M+H$^+$].

Step (vi): Preparation of Compound Formula (53)

To the compound of formula (52) ($R_4$=H) (249 mg, 0.95 mmol) was added a 6N solution of hydrochloric acid (4 mL) and the reaction was refluxed for 4 hours. The volatiles were removed under reduced pressure, the crude product was diluted with ammonia in methanol and the inorganic salts were filtered. The filtrate was concentrated under reduced pressure to obtain compound of formula (53) ($R_4$=H) (208 mg). Yield: 100%.

$^1$H-NMR (DMSO-$d_6$): δ 7.56 (bs, 2H), 3.70-3.60 (m, 1H), 2.83-2.70 (m, 1H), 2.68-2.52 (m, 2H), 2.38-2.25 (m, 1H), 2.20-2.02 (m, 4H), 1.90-1.83 (m, 2H), 1.83-1.60 (m, 9H), 1.40-1.30 (m, 2H).

IR (cm$^{-1}$): 3313, 3103, 2985, 2909, 2848, 2523, 1601, 1579, 1495, 1444, 1382, 1217, 1158, 1145, 1068, 1046, 1031, 877.

Mass (m/z): 221 [M+H$^+$].

Preparation 10

Preparation of Compound of Formula (59)

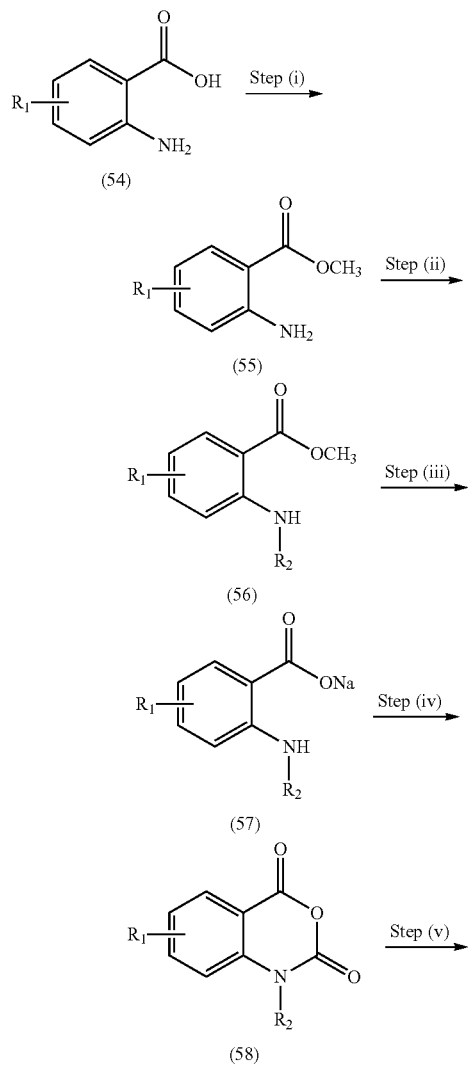

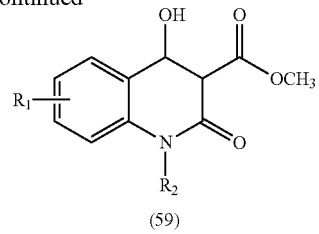

Step (i): Preparation of Compound of Formula (55)

To a stirred solution of compound of formula (54) ($R_1$=H) (12.9 grams, 94.06 mmol) in methanol (188 mL) cooled at 0° C. was added thionyl chloride (27.4 mL, 376.2 mmol) over a period of 30 minutes. The reaction mixture was gradually warmed to room temperature then refluxed for 18 hours. The volatiles were removed under reduced pressure; the residue was diluted with ethylacetate and cooled to ice-bath temperature. A 10% aqueous solution of sodium bicarbonate was added and the two layers were separated. The organic layer was washed with brine, dried over anhydrous sodium sulphate and the solvent was removed under reduced pressure to obtain compound of formula (55) ($R_1$=H) (12.2 grams, 85.8% yield).

$^1$H-NMR (CDCl$_3$): δ 7.86 (d, J=8.0 Hz, 1H), 7.27 (t, J=8.4 Hz, 1H), 6.70-6.60 (m, 2H), 5.90-5.50 (bs, 2H), 3.87 (s, 3H).

Mass (m/z): 152 [M+H$^+$].

Step (ii): Preparation of Compound Formula (56)

To a stirred solution of compound of formula (55) ($R_1$=H) (13.2 grams, 87.3 mmol) in dichloromethane (174 mL) cooled at 0° C. was added acetic acid (10 mL, 174 mmol) and 2,2-dimethoxypropane (64.1 mL, 523.6 mmol). After stirring for 15 minutes at the same temperature, sodium triacetoxyborohydride (30.3 grams, 143.2 mmol) was added and the reaction mixture was gradually warmed to room temperature and stirred for 16 hours. The reaction mixture was diluted with dichloromethane and washed with 10% aqueous sodium bicarbonate solution, brine, dried over anhydrous sodium sulphate and the solvent was removed under reduced pressure. The crude product was purified by silica gel flash column chromatography to obtain compound of formula (56) ($R_1$=H, $R_2$=isopropyl) (12.2 grams). Yield: 73%.

$^1$H-NMR (CDCl$_3$): δ 7.90 (d, J=8.0 Hz, 1H), 7.69 (bs, 1H), 7.34 (t, J=8.5 Hz, 1H), 6.71 (d, J=8.5 Hz, 1H), 6.55 (t, J=7.5 Hz, 1H), 3.85 (s, 3H), 3.80-3.65 (m, 1H), 1.27 (d, J=6.3 Hz, 6H).

Mass (m/z): 194 [M+H$^+$].

Step (iii): Preparation of Compound Formula (57)

To a stirred solution of compound of formula (56) ($R_1$=H, $R_2$=isopropyl) (12.2 grams, 63.1 mmol) in 1:2 mixture of methanol and water (126 mL) cooled at 0° C. was added sodium hydroxide (2.5 grams, 63.1 mmol). The reaction mixture was gradually warmed to room temperature and then refluxed for 16 hours. The volatiles were removed under reduced pressure and the residue was dried under vacuum at 70° C. for several hours to obtain compound of formula (57) ($R_1$=H, $R_2$=isopropyl) (12.4 grams). Yield: 97.7%.

$^1$H NMR (D$_2$O): δ 7.62 (d, J=8.0 Hz, 1H), 7.25 (t, J=8.3 Hz, 1H), 6.81 (d, J=8.3 Hz, 1H), 6.65 (t, J=7.5 Hz, 1H), 3.62-3.50 (m, 1H), 1.07 (d, J=6.2 Hz, 6H).

Mass (m/z): 178 [M-H$^{30}$].

Step (iv): Preparation of Compound Formula (58)

To a stirred suspension of compound of formula (57) ($R_1$=H, $R_2$=isopropyl) (5.1 grams, 25.3 mmol) in dry dichloromethane (25 mL) cooled at 0° C. was added triphosgene (15 grams, 50.56 mmol). The reaction mixture was gradually warmed to room temperature and stirred for 16 hours. Water and dichloromethane were added and the two layers were separated. The organic layer was washed with aqueous sodium bicarbonate, brine, dried over anhydrous sodium sulphate and the solvent was removed under reduced pressure to obtain compound of formula (58) ($R_1$=H, $R_2$=isopropyl) (6.25 grams, crude mass), which was taken up for the next reaction without further purification.

$^1$H-NMR (CDCl$_3$): δ 8.18 (d, J=8.0 Hz, 1H), 7.74 (t, J=8.3 Hz, 1H), 7.33 (d, J=8.3 Hz, 1H), 7.28 (t, J=7.5 Hz, 1H), 4.82-4.75 (m, 1H), 1.62 (d, J=6.2 Hz, 6H).

Mass (m/z): 206 [M+H$^+$].

Step (v): Preparation of Compound Formula (59)

To a stirred solution of compound of formula (58) ($R_1$=H, $R_2$=isopropyl) (6.25 grams, crude mass obtained in the foregoing reaction) in dry dimethylformamide cooled at 0° C. was added dimethylmalonate (5.2 mL, 45.6 mmol) and sodium hydride (60% dispersed in mineral oil, 2.0 grams, 50.2 mmol). The reaction mixture was stirred at room temperature then at 100° C. for 2 hours. The solvent was removed under reduced pressure and the crude mass was diluted with ice-water mixture. Thus obtained mixture was acidified with concentrated hydrochloric acid solution and extracted with dichloromethane. The combined organic layer was washed with brine, dried over anhydrous sodium sulphate and the solvent was removed under reduced pressure. The crude product was purified by silica gel flash column chromatography to obtain compound of formula (59) ($R_1$=H, $R_2$=isopropyl) (2.6 grams) Yield: 39% for 2 steps.

$^1$H-NMR (CDCl$_3$): δ 14.05 (s, 1H), 8.22 (d, J=8.0 Hz, 1H), 7.64 (t, J=8.4 Hz, 1H), 7.51 (d, J=8.5 Hz, 1H), 7.23 (t, J=7.5 Hz, 1H), 5.90-5.10 (bs, 1H), 4.04 (s, 3H), 1.63 (d, J=6.2 Hz, 6H).

Mass (m/z): 262 [M+H$^+$].

Example 1

Preparation of N-[(2-Azatricyclo[3.3.1.1$^{3,7}$]dec-2-yl)propyl]-4-hydroxy-1-isopropyl-2-oxo-1,2-dihydroquinoline-3-carboxamide hydrochloride To a stirred solution of compound of formula (59) ($R_1$=H, $R_2$=isopropyl) (305 mg, 1.15 mmol) in toluene (11 mL) was added of compound of formula (8) (453.6 mg, 2.29 mmol) and the reaction mixture was refluxed for 2 hours. The volatiles were removed under reduced pressure and the crude product was purified by silica gel flash column chromatography and the product was treated with isopropanolic HCl to obtain N-[(2-Azatricyclo[3.3.1.1$^{3,7}$]dec-2-yl)propyl]-4-hydroxy-1-isopropyl-2-oxo-1,2-dihydroquinoline-3-carboxamide hydrochloride (384 mg). Yield: 77%.

$^1$H-NMR (DMSO-d$_6$): δ 17.26 (s, 1H), 10.44 (bs, 1H), 9.33 (bs, 1H), 8.10 (d, J=7.8 Hz, 1H), 7.83 (d, J=8.7 Hz, 1H), 7.76 (t, J=8.2 Hz, 1H), 7.35 (t, J=7.5 Hz, 1H), 5.50-5.10 (bs, 1H), 3.60 (bs, 2H), 3.50-3.40 (m, 2H), 3.40-3.30 (m, 2H), 2.25-2.10 (m, 4H), 2.05-1.90 (m, 6H), 1.78 (bs, 2H), 1.75-1.68 (m, 2H), 1.55 (d, J=6.9 Hz, 6H);

IR (cm$^{-1}$): 3425, 3220, 2938, 2724, 2635, 2571, 2500, 1640, 1571, 1499, 1416, 1335, 1189, 1008, 761;

Mass (m/z): 424 [M+H$^+$].

Example 2

Preparation of N-[(2-Azatricyclo[3.3.1.1$^{3,7}$]dec-2-yl)propyl]-4-hydroxy-1-isobutyl-2-oxo-1,2-dihydroquinoline-3-carboxamide hydrochloride To a stirred solution of compound of formula (59) ($R_1$=H, $R_2$=isobutyl) (141 mg, 0.54 mmol) in toluene (5 mL) was added potassium carbonate (71.3 mg, 0.512 mmol) and compound of formula (8) (100.1 mg, 0.512 mmol) and the reaction mixture was refluxed for 3 hours. The volatiles were removed under reduced pressure and the crude product was purified by silica gel flash column chromatography and the product was treated with isopropanolic HCl to obtain N-[(2-Azatricyclo[3.3.1.1$^{3,7}$]dec-2-yl)propyl]-4-hydroxy-1-isobutyl-2-oxo-1,2-dihydroquinoline-3-carboxamide hydrochloride (159.4 mg). Yield: 68%.

$^1$H-NMR (DMSO-d$_6$): δ 17.32 (s, 1H), 10.45 (bs, 1H), 9.35 (bs, 1H), 8.10 (d, J=7.9 Hz, 1H), 7.79 (t, J=8.1 Hz, 1H), 7.66 (d, J=8.7 Hz, 1H), 7.36 (t, J=7.5 Hz, 1H), 4.15 (d, J=6.7 Hz, 2H), 3.65-3.58 (m, 2H), 3.50-3.40 (m, 2H), 3.40-3.25 (m, 2H), 2.25-2.05 (m, 5H), 2.05-1.87 (m, 6H), 1.78 (bs, 2H), 1.72-1.65 (m, 2H), 0.90 (d, J=6.6 Hz, 6H).

IR (cm$^{-1}$): 3397, 3218, 2950, 2936, 2439, 1642, 1569, 1499, 1413, 1183, 1017, 763, 670.

Mass (m/z): 438 [M+H$^+$].

Example 3

Preparation of N-[1-(Tricyclo[3.3.1.1$^{3,7}$]dec-2-yl)pyrrolidin-3-yl]-4-hydroxy-1-isopropyl-2-oxo-1,2-dihydroquinoline-3-carboxamide To a stirred solution of formula (59) ($R_1$=H, $R_2$=isopropyl) (108.3 mg, 0.41 mmol) in dry dimethylformamide (2.5 mL) was added potassium carbonate (57 mg, 0.42 mmol), compound of formula (53) (100 mg, 0.45 mmol) and the reaction was heated to 130-135° C. for 18 hours. The reaction was cooled to 0° C., diluted with water and extracted with ether. The combined organic layer was washed with brine, dried over anhydrous sodium sulphate and the solvent was removed under reduced pressure. The crude product was purified by silica gel flash column chromatography to obtain N-[1-(Tricyclo[3.3.1.1$^{3,7}$]dec-2-yl)pyrrolidin-3-yl]-4-hydroxy-1-isopropyl-2-oxo-1,2-dihydroquinoline-3-carboxamide (54 mg). Yield: 29%.

$^1$H-NMR (CDCl$_3$): δ 17.16 (s, 1H), 10.60 (bs, 1H), 8.23 (d, J=7.8 Hz, 1H), 7.75-7.50 (m, 2H), 7.40-7.20 (m, 1H), 5.80-5.10 (bs, 1H), 4.65-4.52 (m, 1H), 2.90-2.75 (m, 2H), 2.70-2.60 (m, 1H), 2.55-2.42 (m, 1H), 2.40-2.15 (m, 4H), 2.0-1.90 (m, 2H), 1.90-1.75 (m, 4H), 1.75-1.20 (m, 7H), 1.64 (d, J=7.0 Hz, 6H);

IR (cm$^{-1}$): 3190, 2904, 2848, 2786, 1910, 1639, 1547, 1410, 1323, 1172, 995, 747, 704.

Mass (m/z): 450 [M+H$^+$].

Examples 4-27

The compounds of Examples 4-27 were prepared by following the procedures as described in Examples 1 to 3, with some non-critical variations

| | |
|---|---|
| 4. N-[(5-Hydroxy-2-azatricyclo[3.3.1.1$^{3,7}$]dec-2-yl)propyl]-4-hydroxy-1-isopropyl-2-oxo-1,2-dihydroquinoline-3-carboxamide | $^1$H-NMR (CDCl$_3$): δ 17.26 (s, 1H), 10.42 (bs, 1H), 8.10 (d, J = 7.8 Hz, 1H), 7.83 (d, J = 8.7 Hz, 1H), 7.76 (t, J = 8.2 Hz, 1H), 7.35 (t, J = 7.4 Hz, 1H), 5.40-5.10 (bs, 1H), 5.0 (bs, 1H), 3.85-3.72 (m, 2H), 3.50-3.40 (m, 2H), 3.30- |

| | -continued |
|---|---|
| | 3.20 (m, 2H), 2.25-1.90 (m, 7H), 1.80-1.70 (m, 4H), 1.65-1.50 (m, 2H), 1.55 (d, J = 6.8 Hz, 6H).<br>IR (cm$^{-1}$): 3482, 3425, 2943, 2872, 2483, 1638, 1572, 1419, 1338, 1190, 1140, 1108, 1020, 762.<br>Mass (m/z): 440 [M + H$^+$]. |
| 5. N-[(5-Phenyl-2-azatricyclo[3.3.1.1$^{3,7}$]dec-2-yl) propyl]-4-hydroxy-1-isopropyl-2-oxo-1,2-dihydroquinoline-3-carboxamide hydrochloride | $^1$H-NMR (DMSO-d$_6$): δ 17.28 (bs, 1H), 10.45 (bs, 1H), 9.84 (bs, 0.5H), 9.70 (bs, 0.5H), 8.10 (d, J = 7.7 Hz, 1H), 7.90-7.70 (m, 2H), 7.42-7.35 (m, 4H), 7.30-7.20 (m, 5H), 5.70-5.10 (bs, 1H), 3.88-3.80 (m, 2H), 3.54-3.30 (m, 4H), 2.48-1.93 (m, 12H), 1.80-1.70 (m, 1H), 1.55 (d, J = 7.4 Hz, 3H), 1.53 (d, J = 7.3 Hz, 3H);<br>IR (cm$^{-1}$): 3419, 3223, 2938, 2572, 2504, 1632, 1567, 1497, 1447, 1401, 1333, 1173, 1109, 1004, 808, 758, 701;<br>Mass (m/z): 499 [M + H$^+$]. |
| 6. N-[(1,4-Diazatricyclo[4.3.1.1$^{3,8}$]undec-4-yl) propyl]-4-hydroxy-1-isopropyl-2-oxo-1,2-dihydro-quinoline-3-carboxamide | $^1$H-NMR (CDCl$_3$): δ 16.68 (s, 1H), 10.54 (bs, 1H), 8.17 (d, J = 8.0 Hz, 1H), 7.61 (t, J = 7.6 Hz, 1H), 7.53 (d, J = 9.0 Hz, 1H), 7.24 (t, J = 7.6 Hz, 1H), 5.80-5.70 (m, 1H), 4.30-3.80 (m, 6H), 3.65-3.50 (m, 6H), 2.85-2.75 (m, 1H), 2.70-2.60 (m, 1H), 2.45-2.15 (m, 5H), 2.10-2.0 (m, 2H), 1.62 (d, J = 7.0 Hz, 6H).<br>IR (cm$^{-1}$): 3482, 3425, 2943, 2872, 2483, 1638, 1572, 1419, 1338, 1190, 1140, 1108, 1020, 762.<br>Mass (m/z): 439 [M + H$^+$]. |
| 7. N-[(2-Azatricyclo[3.3.1.1$^{3,7}$]dec-2-yl) propyl]-4-hydroxy-1-isobutyl-6-methoxy-2-oxo-1,2-dihydroquinoline-3-carboxamide | $^1$H-NMR (CDCl$_3$): δ 17.17 (bs, 1H), 10.57 (bs, 1H), 7.63 (s, 1H), 7.50 (d, J = 8.9 Hz, 1H), 7.24 (d, J = 8.9 Hz, 1H), 5.80-5.10 (bs, 1H), 3.90 (s, 3H), 3.70-3.45 (m, 2H), 3.30-2.70 (m, 4H), 2.40-1.90 (m, 6H), 1.90-1.75 (m, 4H), 1.70-1.40 (m, 10H).<br>IR (cm$^{-1}$): 3192, 2910, 2860, 2782, 1612, 1544, 1410, 1312, 1189, 995, 756, 703.<br>Mass (m/z): 454, 460 [M + H$^+$]. |
| 8. N-[(2-Azatricyclo[3.3.1.1$^{3,7}$]dec-2-yl) propyl]-6-chloro-4-hydroxy-1-isopropyl-2-oxo-1,2-dihydroquinoline-3-carboxamide | $^1$H-NMR (CDCl$_3$): δ 17.36 (bs, 1H), 10.36 (bs, 1H), 8.20 (s, 1H), 7.60-7.48 (m, 2H), 5.60-5.10 (bs, 1H), 3.70-3.50 (m, 2H), 3.15-2.70 (m, 4H), 2.40-1.96 (m, 6H), 1.96-1.80 (m, 4H), 1.70-1.30 (m, 10H).<br>IR (cm$^{-1}$): 3170, 2911, 2848, 2775, 1639, 1538, 1408, 1311, 1172, 990, 757, 701.<br>Mass (m/z): 458, 460 [M + H$^+$]. |
| 9. N-[(2-Azatricyclo[3.3.1.1$^{3,7}$]dec-2-yl) propyl]-6-fluoro-4-hydroxy-1-isopropyl-2-oxo-1,2-dihydroquinoline-3-carboxamide | $^1$H-NMR (CDCl$_3$): δ 17.11 (bs, 1H), 10.47 (bs, 1H), 7.88 (d, J = 6.1 Hz, 1H), 7.53 (s, 1H), 7.40-7.34 (m, 1H), 5.70-5.10 (bs, 1H), 3.60-3.45 (m, 2H), 3.30-2.80 (m, 4H), 2.40-2.0 (m, 6H), 1.90-1.40 (m, 14H).<br>IR (cm$^{-1}$): 3192, 2898, 2862, 2786, 1910, 1618, 1544, 1408, 1343, 1172, 995, 756, 699.<br>Mass (m/z): 442 [M + H$^+$]. |
| 10. N-[(2-Azatricyclo[3.3.1.1$^{3,7}$]dec-2-yl) propyl]-6-bromo-4-hydroxy-1-isopropyl-2-oxo-1,2-dihydroquinoline-3-carboxamide | $^1$H-NMR (CDCl$_3$): δ 17.33 (s, 1H), 10.37 (bs, 1H), 8.35 (s, 1H), 7.69 (d, J = 9.1 Hz, 1H), 7.43 (d, J = 9.1 Hz, 1H), 5.70-5.10 (bs, 1H), 3.60-3.50 (m, 2H), 3.25-2.75 (m, 4H), 2.40-2.0 (m, 6H), 1.98-1.50 (m, 14H).<br>IR (cm$^{-1}$): 3182, 2911, 2872, 2785, 1911, 1622, 1535, 1410, 1323, 1172, 995, 756, 703.<br>Mass (m/z): 502, 504 [M + H$^+$]. |
| 11. N-[(2-Azatricyclo[3.3.1.1$^{3,7}$]dec-2-yl) propyl]-6-amino-4-hydroxy-1-isopropyl-2-oxo-1,2-dihydroquinoline-3-carboxamide | $^1$H-NMR (CDCl$_3$): δ 17.13 (s, 1H), 10.54 (bs, 1H), 7.48 (s, 1H), 7.39 (d, J = 8.8 Hz, 1H), 7.02 (d, J = 8.8 Hz, 1H), 5.80-5.10 (bs, 1H), 3.80-3.70 (m, 2H), 3.55-3.46 (m, 2H), 2.98-2.90 (m, 2H), 2.90-2.78 (m, 2H), 2.18-2.08 (m, 4H), 2.05-1.97 (m, 2H), 1.90-1.50 (m, 14H).<br>IR (cm$^{-1}$): 3191, 2903, 2847, 2785, 1908, 1638, 1546, 1406, 1323, 1179, 997, 757, 701.<br>Mass (m/z): 439 [M + H$^+$]. |
| 12. N-[2-(Pyridin-3-yl methyl)-1-azabicyclo[2.2.2]oct-3-yl]-4-hydroxy-1-isopropyl-2-oxo-1,2-dihydroquinoline-3-carboxamide | $^1$H-NMR (CDCl$_3$): δ 16.92 (s, 1H), 10.72 (bd, 1H), 8.50 (s, 1H), 8.36 (d, J = 3.5 Hz, 1H), 8.24 (d, J = 7.8 Hz, 1H), 7.70-7.55 (m, 3H), 7.30-7.20 (m, 2H), 7.20-7.10 (m, 1H), 5.80-5.30 (bs, 1H), 3.95-3.85 (m, 1H), 3.15-3.05 (m, 1H), 3.05-2.80 (m, 5H), 2.80-2.70 (m, 1H), 2.08-2.0 (m, 1H), 1.88-1.45 (m, 4H), 1.66 (d, J = 7.2 Hz, 6H).<br>IR (cm$^{-1}$): 3164, 2901, 2842, 2781, 1919, 1633, 1544, 1412, 1320, 1179, 990, 757, 699.<br>Mass (m/z): 447 [M + H$^+$]. |
| 13. N-[2-(Pyridin-2-yl methyl)-1-azabicyclo[2.2.2]oct-3-yl]-4-hydroxy-1-isopropyl-2-oxo-1,2-dihydroquinoline-3-carboxamide | $^1$H-NMR (CDCl$_3$): δ 16.81 (s, 1H), 10.67 (bs, 1H), 8.45 (d, J = 4.5 Hz, 1H), 8.21 (d, J = 7.3 Hz, 1H), 7.70-7.45 (m, 3H), 7.30-7.20 (m, 2H), 7.0-6.92 (m, 1H), 5.90-5.40 (bs, 1H), 4.08-3.98 (m, 1H), 3.45-3.30 (m, 1H), 3.30-3.0 (m, 5H), 3.0-2.82 (m, 1H), 2.12-2.05 (m, 1H), 1.98-1.70 (m, 3H), 1.64 (d, J = 7.1 Hz, 6H), 1.65-1.55 (m, 1H).<br>IR (cm$^{-1}$): 3424, 2972, 2937, 2801, 2667, 2600, 1963, 1637, 1564, 1493, 1471, 1336, 1167, 944, 779, 762, 752, 717.<br>Mass (m/z): 447 [M + H$^+$]. |

-continued

| | |
|---|---|
| 14. N-(2-Methyl-2-azatricyclo[3.3.1.1³,⁷]dec-5-yl)-4-hydroxy-1-isopropyl-2-oxo-1,2-dihydro-quinoline-3-carboxamide | ¹H-NMR (CDCl₃): δ 17.26 (s, 1H), 10.45 (bs, 1H), 8.24 (d, J = 7.8 Hz, 1H), 7.70-7.55 (m, 2H), 7.26 (t, J = 7.8 Hz, 1H), 5.80-5.30 (bs, 1H), 3.20-3.10 (m, 2H), 2.70-2.50 (m, 6H), 2.25-2.05 (m, 4H), 2.03-1.95 (m, 2H), 1.85-1.40 (m, 2H), 1.63 (d, J = 7.1 Hz, 6H).<br>IR (cm⁻¹): 3568, 3560, 3368, 3199, 2928, 2911, 2856, 2162, 1933, 1636, 1555, 1336, 1307, 1185, 1017, 805, 746, 721.<br>Mass (m/z): 396 [M + H⁺]. |
| 15. N-(2-Isopropyl-2-azatricyclo[3.3.1.1³,⁷]dec-5-yl)-4-hydroxy-1-isopropyl-2-oxo-1,2-dihydro-quinoline-3-carboxamide | ¹H-NMR (CDCl₃): δ 17.30 (s, 1H), 10.45 (bs, 1H), 8.24 (d, J = 7.8 Hz, 1H), 7.70-7.55 (m, 2H), 7.26 (t, J = 7.2 Hz, 1H), 5.90-5.10 (bs, 1H), 3.70-3.40 (m, 2H), 3.30-3.10 (m, 1H), 2.65-2.40 (m, 2H), 2.35-2.20 (m, 4H), 2.10-1.90 (m, 3H), 1.80-1.50 (m, 14H).<br>IR (cm⁻¹): 3178, 2922, 2819, 2772, 1933, 1621, 1512, 1421, 1319, 1167, 989, 757, 701.<br>Mass (m/z): 424 [M + H⁺]. |
| 16. N-(2-Benzyl-1-azabicyclo[2.2.2]oct-3-yl)-4-hydroxy-1-isopropyl-2-oxo-1,2-dihydroquinoline-3-carboxamide | ¹H-NMR (CD₃OD): δ 10.66 (bs, 1H), 8.18 (d, J = 7.9 Hz, 1H), 7.85-7.75 (m, 2H), 7.40-7.30 (m, 3H), 7.30-7.20 (m, 2H), 7.10-7.02 (m, 1H), 5.70-5.10 (bs, 1H), 4.40-4.30 (m, 1H), 3.90-3.80 (m, 1H), 3.75-3.55 (m, 2H), 3.50-3.35 (m, 2H), 3.25-3.10 (m, 2H), 2.40-2.25 (m, 1H), 2.25-2.05 (m, 3H), 2.05-1.97 (m, 1H), 1.61 (d, J = 6.8 Hz, 6H).<br>IR (cm⁻¹): 3182, 2909, 2871, 2745, 1912, 1623, 1538, 1417, 1312, 1183, 990, 756, 700.<br>Mass (m/z): 446 [M + H⁺]. |
| 17. N-[(2-Azatricyclo[3.3.1.1³,⁷]dec-2-yl)ethyl]-4-hydroxy-1-isopropyl-2-oxo-1,2-dihydroquinoline-3-carboxamide hydrochloride | ¹H-NMR (DMSO-d₆): δ 16.96 (s, 1H), 10.48 (bs, 1H), 9.45 (bs, 1H), 8.11 (d, J = 7.2 Hz, 1H), 7.84 (d, J = 8.7 Hz, 1H), 7.77 (t, J = 7.2 Hz, 1H), 7.36 (t, J = 7.4 Hz, 1H), 5.50-5.10 (bs, 1H), 3.85-3.65 (m, 4H), 3.50-3.40 (m, 2H), 2.30-2.10 (m, 4H), 2.05-1.85 (m, 4H), 1.82-1.65 (m, 4H), 1.56 (d, J = 6.9 Hz, 6H).<br>IR (cm⁻¹): 3360, 3176, 2932, 2470, 1637, 1566, 1492, 1450, 1410, 1174, 1013, 803, 752.<br>Mass (m/z): 410 [M + H⁺]. |
| 18. N-(2-Butyl-2-azatricyclo[3.3.1.1³,⁷]dec-5-yl)-4-hydroxy-1-isopropyl-2-oxo-1,2-dihydroquinoline-3-carboxamide hydrochloride | ¹H-NMR (DMSO-d₆): δ 17.0 (s, 1H), 10.64 (bs, 1H), 9.90 (bs, 0.5H), 9.80 (bs, 0.5H), 8.10 (d, J = 8.0 Hz, 1H), 7.84 (d, J = 8.8 Hz, 1H), 5.70-5.10 (bs, 1H), 7.77 (t, J = 7.4 Hz, 1H), 7.36 (t, J = 7.5 Hz, 1H), 3.85-3.75 (m, 2H), 3.33-3.23 (m, 2H), 2.76-2.68 (m, 1H), 2.62-2.52 (m, 1H), 2.40-2.30 (m, 1H), 2.30-2.15 (m, 6H), 1.95-1.88 (m, 1H), 1.75-1.60 (m, 3H), 1.55 (d, J = 6.9 Hz, 6H), 1.42-1.32 (m, 2H), 0.92 (t, J = 7.3 Hz, 3H).<br>IR (cm⁻¹): 3334, 3119, 2954, 2466, 1645, 1571, 1487, 1442, 1410, 1166, 1019, 801, 756.<br>Mass (m/z): 438 [M + H⁺]. |
| 19. N-(2-Ethyl-2-azatricyclo[3.3.1.1³,⁷]dec-5-yl methyl)-4-hydroxy-1-isopropyl-2-oxo-1,2-dihydroquinoline-3-carboxamide hydrochloride | ¹H-NMR (DMSO-d₆): δ 17.29 (s, 1H), 10.53 (bs, 1H), 9.56 (bs, 0.5H), 9.24 (bs, 0.5H), 8.12 (d, J = 7.8 Hz, 1H), 7.84 (d, J = 8.6 Hz, 1H), 7.77 (t, J = 7.2 Hz, 1H), 7.36 (t, J = 7.4 Hz, 1H), 5.70-5.15 (bs, 1H), 3.72-3.65 (m, 2H), 3.30-3.20 (m, 4H), 2.20-1.95 (m, 5H), 1.85-1.70 (m, 3H), 1.70-1.50 (m, 3H), 1.55 (d, J = 6.8 Hz, 6H), 1.23 (t, J = 7.0 Hz, 3H).<br>IR (cm⁻¹): 3368, 3166, 2945, 2480, 1640, 1572, 1487, 1448, 1410, 1174, 1012, 803, 756.<br>Mass (m/z): 424 [M + H⁺]. |
| 20. N-(1-Butyl piperidin-4-yl)-4-hydroxy-1-isopropyl-2-oxo-1,2-dihydroquinoline-3-carboxamide hydrochloride | ¹H-NMR (DMSO-d₆): δ 17.03 (s, 1H), 10.44 (bs, 1H), 9.89 (bs, 1H), 8.11 (d, J = 8.0 Hz, 1H), 7.84 (d, J = 8.8 Hz, 1H), 7.77 (t, J = 7.2 Hz, 1H), 7.36 (t, J = 7.4 Hz, 1H), 5.70-5.10 (bs, 1H), 4.15-4.0 (m, 1H), 3.60-3.50 (m, 2H), 3.15-2.98 (m, 4H), 2.20-2.10 (m, 2H), 1.95-1.80 (m, 2H), 1.70-1.58 (m, 2H), 1.54 (d, J = 6.8 Hz, 6H), 1.40-1.25 (m, 2H), 0.91 (t, J = 6.9 Hz, 3H).<br>IR (cm⁻¹): 3494, 3389, 2962, 2936, 2646, 2530, 1636, 1567, 1399, 1251, 1174, 949, 768, 752.<br>Mass (m/z): 386 [M + H⁺]. |
| 21. N-[(1-(Pyrrolidin-1-yl)tricyclo[3.3.1.0³,⁷]nonan-3-yl]-4-hydroxy-1-isopropyl-2-oxo-1,2-dihydro-quinoline-3-carboxamide | ¹H-NMR (CDCl₃): δ 17.34 (bs, 1H), 10.62 (bs, 1H), 8.25 (d, J = 7.8 Hz, 1H), 7.70-7.50 (m, 2H), 7.30-7.20 (m, 1H), 5.90-5.10 (bs, 1H), 3.0-2.70 (m, 2H), 2.70-2.63 (m, 1H), 2.60-2.35 (m, 3H), 2.18-1.70 (m, 10H), 1.70-1.45 (m, 10H).<br>IR (cm⁻¹): 3424, 3230, 2952, 2604, 2485, 1636, 1561, 1412, 1334, 1184, 767, 702.<br>Mass (m/z): 436 [M + H⁺]. |

| | -continued |
|---|---|
| 22. N-[(2-Azatricyclo[3.3.1.1³,⁷]dec-2-yl)propyl]-6-nitro-4-hydroxy-1-isopropyl-2-oxo-1,2-dihydroquinoline-3-carboxamide | $^1$H-NMR (CDCl$_3$): δ 17.10 (bs, 1H), 10.25 (bs, 1H), 9.11 (d, J = 2.6 Hz, 1H), 8.42 (dd, J = 9.4, 2.6 Hz, 1H), 7.63 (d, J = 9.4 Hz, 1H), 5.70-5.10 (bs, 1H), 3.60-3.50 (m, 2H), 3.02-2.90 (m, 2H), 2.90-2.78 (m, 2H), 2.20-2.08 (m, 4H), 2.06-1.96 (m, 2H), 1.90-1.80 (m, 4H), 1.64 (d, J = 7.0 Hz, 6H), 1.60-1.50 (m, 4H).<br>Mass (m/z): 469 [M + H$^+$]. |
| 23. N-(2-Azatricyclo[3.3.1.1³,⁷]dec-5-yl)-4-hydroxy-1-isopropyl-2-oxo-1,2-dihydroquinoline-3-carboxamide hydrochloride | $^1$H-NMR (D$_2$O): δ 7.94 (d, J = 7.7 Hz, 1H), 7.73 (d, J = 8.5 Hz, 1H), 7.60 (t, J = 7.4 Hz, 1H), 7.26 (t, J = 7.4 Hz, 1H), 5.40-5.20 (bs, 1H), 5.0-4.90 (bs, 1H), 4.10-4.0 (m, 1H), 3.90-3.84 (m, 1H), 2.37-2.25 (m, 1H), 2.20-2.02 (m, 2H), 2.02-1.70 (m, 10H), 1.46 (d, J = 6.8 Hz, 6H).<br>Mass (m/z): 382 [M + H$^+$]. |
| 24. N-[(2-Azatricyclo[3.3.1.1³,⁷]dec-2-yl)propyl]-4-hydroxy-1-methyl-2-oxo-1,2-dihydroquinoline-3-carboxamide hydrochloride | $^1$H-NMR (DMSO-d$_6$): δ 17.28 (bs, 1H), 10.44 (bs, 1H), 9.48 (bs, 1H), 8.10 (d, J = 7.2 Hz, 1H), 7.80 (t, J = 7.3 Hz, 1H), 7.63 (d, J = 8.6 Hz, 1H), 7.38 (t, J = 7.5 Hz, 1H), 3.63 (s, 3H), 3.62-3.56 (m, 2H), 3.52-3.40 (m, 2H), 3.35-3.20 (m, 2H), 2.23-2.12 (m, 4H), 2.07-1.88 (m, 6H), 1.80-1.75 (m, 2H), 1.75-1.65 (m, 2H).<br>Mass (m/z): 396 [M + H$^+$]. |
| 25. N-[(2-Azatricyclo[3.3.1.1³,⁷]dec-2-yl)propyl]-1-benzyl-4-hydroxy-2-oxo-1,2-dihydroquinoline-3-carboxamide hydrochloride | $^1$H-NMR (DMSO-d$_6$): δ 17.45 (bs, 1H), 10.39 (bs, 1H), 9.31 (bs, 1H), 8.12 (d, J = 7.0 Hz, 1H), 7.70 (t, J = 7.2 Hz, 1H), 7.48 (d, J = 8.6 Hz, 1H), 7.45-7.30 (m, 3H), 7.30-7.15 (m, 3H), 5.60-5.50 (bs, 2H), 3.66-3.58 (m, 2H), 3.53-3.42 (m, 2H), 3.40-3.25 (m, 2H), 2.27-2.10 (m, 4H), 2.05-1.88 (m, 6H), 1.83-1.77 (m, 2H), 1.75-1.65 (m, 2H).<br>Mass (m/z): 472 [M + H$^+$]. |
| 26. N-[(4-(Morpholin-4-yl)cyclohexyl)-4-hydroxy-1-isopropyl-2-oxo-1,2-dihydroquinoline-3-carboxamide hydrochloride | $^1$H-NMR (DMSO-d$_6$): δ 17.29 (bs, 1H), 10.48 (bs, 1H), 10.35 (bs, 1H), 8.10 (d, J = 7.4 Hz, 1H), 7.83 (d, J = 8.7 Hz, 1H), 7.76 (t, J = 7.2 Hz, 1H), 7.35 (t, J = 7.4 Hz, 1H), 5.70-5.10 (bs, 1H), 4.0-3.93 (m, 2H), 3.88-3.75 (m, 3H), 3.45-3.30 (m, 2H), 3.30-3.18 (m, 2H), 3.18-3.03 (m, 2H), 2.25-2.05 (m, 4H), 1.75-1.55 (m, 2H), 1.55 (d, J = 6.9 Hz, 6H), 1.50-1.35 (m, 2H).<br>IR (cm$^{-1}$): 3504, 3383, 3235, 2938, 2867, 2603, 1633, 1566, 1455, 1405, 1340, 1176, 1126, 988, 772.<br>Mass (m/z): 414 [M + H$^+$]. |
| 27. N-(4-(Pyrrolidin-1-yl) cyclohexyl)-4-hydroxy-1-isopropyl-2-oxo-1,2-dihydroquinoline-3-carboxamide hydrochloride | $^1$H-NMR (DMSO-d$_6$): δ 17.28 (bs, 1H), 11.25 (bs, 1H), 10.35 (bs, 1H), 8.10 (d, J = 7.0 Hz, 1H), 7.83 (d, J = 8.6 Hz, 1H), 7.74 (t, J = 7.0 Hz, 1H), 7.35 (t, J = 7.4 Hz, 1H), 5.70-5.10 (bs, 1H), 3.90-3.76 (m, 1H), 3.56-3.45 (m, 2H), 3.20-3.0 (m, 3H), 2.20-1.90 (m, 6H), 1.90-1.80 (m, 2H), 1.54 (d, J = 7.0 Hz, 6H), 1.60-1.45 (m, 4H).<br>IR (cm$^{-1}$): 3416, 3217, 2930, 2775, 1636, 1563, 1453, 1410, 1335, 1177, 746.<br>Mass (m/z): 398 [M + H$^+$]. |

Examples 28-71

The person skilled in the art can prepare the compounds of Examples 28-71 by following the procedures described above.

28. N-(2-Methyl-2-azatricyclo[3.3.1.1³,⁷]dec-5-yl)-4-hydroxy-1-isopropyl-2-oxo-1,2-dihydroquinoline-3-carboxamide
29. N-(2-Methyl-2-azatricyclo[3.3.1.1³,⁷]dec-5-yl)-1-cyclopropyl-4-hydroxy-2-oxo-1,2-dihydroquinoline-3-carboxamide
30. N-(2-Methyl-2-azatricyclo[3.3.1.1³,⁷]dec-5-yl)-4-hydroxy-1-isobutyl-2-oxo-1,2-dihydroquinoline-3-carboxamide
31. N-[2-(Pyridin-2-ylmethyl)-1-azabicyclo[2.2.2]oct-3-yl]-4-hydroxy-1-isopropyl-2-oxo-1,2-dihydroquinoline-3-carboxamide
32. N-[2-(Pyridin-2-ylmethyl)-1-azabicyclo[2.2.2]oct-3-yl]-1-cyclopropyl-4-hydroxy-2-oxo-1,2-dihydroquinoline-3-carboxamide
33. N-[2-(Pyridin-2-ylmethyl)-1-azabicyclo[2.2.2]oct-3-yl]-4-hydroxy-1-isobutyl-2-oxo-1,2-dihydroquinoline-3-carboxamide
34. N-[(2-Azatricyclo[3.3.1.1³,⁷]dec-2-yl)propyl]-1-cyclopropyl-4-hydroxy-2-oxo-1,2-dihydroquinoline-3-carboxamide
35. N-[(2-Azatricyclo[3.3.1.1³,⁷]dec-2-yl)propyl]-1-benzyl-4-hydroxy-2-oxo-1,2-dihydroquinoline-3-carboxamide
36. N-[(2-Azatricyclo[3.3.1.1³,⁷]dec-2-yl)propyl]-4-hydroxy-2-oxo-1-(pyridin-2-ylmethyl)-1,2-dihydroquinoline-3-carboxamide
37. N-[(2-Azatricyclo[3.3.1.1³,⁷]dec-2-yl)propyl]-4-hydroxy-2-oxo-1-(pyridin-3-ylmethyl)-1,2-dihydroquinoline-3-carboxamide
38. N-[(2-Azatricyclo[3.3.1.1³,⁷]dec-2-yl)propyl]-1-cyclopentyl-4-hydroxy-2-oxo-1,2-dihydroquinoline-3-carboxamide -continued 39. N-[(2-Azatricyclo[3.3.1.1$^{3,7}$]dec-2-yl)propyl]-1-cyclohexyl-4-hydroxy-2-oxo-1,2-dihydroquinoline-3-carboxamide
40. N-[(5-Hydroxy-2-azatricyclo[3.3.1.1$^{3,7}$]dec-2-yl)propyl]-1-cyclohexyl-4-hydroxy-2-oxo-1,2-dihydroquinoline-3-carboxamide
41. N-[(5-Hydroxy-2-azatricyclo[3.3.1.1$^{3,7}$]dec-2-yl)propyl]-4-hydroxy-1-isobutyl-2-oxo-1,2-dihydroquinoline-3-carboxamide
42. N-[(5-Hydroxy-2-azatricyclo[3.3.1.1$^{3,7}$]dec-2-yl)propyl]-1-cyclopropyl-4-hydroxy-2-oxo-1,2-dihydroquinoline-3-carboxamide
43. N-[(5-Hydroxy-2-azatricyclo[3.3.1.1$^{3,7}$]dec-2-yl)propyl]-1-cyclopentyl-4-hydroxy-2-oxo-1,2-dihydroquinoline-3-carboxamide
44. N-[(5-Hydroxy-2-azatricyclo[3.3.1.1$^{3,7}$]dec-2-yl)propyl]-4-hydroxy-2-oxo-1-(tetrahydropyran-4-yl)-1,2-dihydroquinoline-3-carboxamide
45. N-[(2-Azatricyclo[3.3.1.1$^{3,7}$]dec-2-yl)propyl]-4-hydroxy-2-oxo-1-(tetrahydropyran-4-yl)-1,2-dihydroquinoline-3-carboxamide
46. N-[(5-Hydroxy-2-azatricyclo[3.3.1.1$^{3,7}$]dec-2-yl)propyl]-1-benzyl-4-hydroxy-2-oxo-1,2-dihydroquinoline-3-carboxamide
47. N-[(5-Hydroxy-2-azatricyclo[3.3.1.1$^{3,7}$]dec-2-yl)propyl]-4-hydroxy-2-oxo-1-(pyridin-2-ylmethyl)-1,2-dihydroquinoline-3-carboxamide
48. N-[(5-Phenyl-2-azatricyclo[3.3.1.1$^{3,7}$]dec-2-yl)propyl]-4-hydroxy-2-oxo-1-(pyridin-2-ylmethyl)-1,2-dihydroquinoline-3-carboxamide
49. N-[(5-Phenyl-2-azatricyclo[3.3.1.1$^{3,7}$]dec-2-yl)propyl]-1-cyclopropyl-4-hydroxy-2-oxo-1,2-dihydroquinoline-3-carboxamide
50. N-[(5-Phenyl-2-azatricyclo[3.3.1.1$^{3,7}$]dec-2-yl)propyl]-4-hydroxy-1-isobutyl-2-oxo-1,2-dihydroquinoline-3-carboxamide
51. N-[(5-Phenyl-2-azatricyclo[3.3.1.1$^{3,7}$]dec-2-yl)propyl]-4-hydroxy-2-oxo-1-(2-methylbenzyl)-1,2-dihydroquinoline-3-carboxamide
52. N-[1-(Tetrahydropyran-4-ylmethyl)piperidin-4-yl]-4-hydroxy-1-isopropyl-2-oxo-1,2-dihydroquinoline-3-carboxamide
53. N-[1-(Tetrahydropyran-4-ylmethyl)piperidin-4-yl]-1-cyclopropyl-4-hydroxy-2-oxo-1,2-dihydroquinoline-3-carboxamide
54. N-[1-(Tetrahydropyran-4-ylmethyl)piperidin-4-yl]-4-hydroxy-1-isobutyl-2-oxo-1,2-dihydroquinoline-3-carboxamide
55. N-[1-(Tetrahydropyran-4-ylmethyl)piperidin-4-yl]-1-benzyl-4-hydroxy-2-oxo-1,2-dihydroquinoline-3-carboxamide
56. N-(1-Phenethyl piperidin-4-yl)-4-hydroxy-1-isopropyl-2-oxo-1,2-dihydroquinoline-3-carboxamide
57. N-[(1-(Pyrrolidin-1-yl) tricyclo[3.3.1.0$^{3,7}$]nonan-3-yl]-1-cyclopropyl-4-hydroxy-2-oxo-1,2-dihydroquinoline-3-carboxamide
58. N-[(1-(Pyrrolidin-1-yl) tricyclo[3.3.1.0$^{3,7}$]nonan-3-yl]-1-cyclohexyl-4-hydroxy-2-oxo-1,2-dihydroxquinoline-3-carboxamide
59. N-[(1-(Pyrrolidin-1-yl) tricyclo[3.3.1.0$^{3,7}$]nonan-3-yl]-1-benzyl-4-hydroxy-2-oxo-1,2-dihydroquinoline-3-carboxamide
60. N-[(1-(Pyrrolidin-1-yl) tricyclo[3.3.1.0$^{3,7}$]nonan-3-yl]--4-hydroxy-2-oxo-1-(pyridin-2-ylmethyl)-1,2-dihydroquinoline-3-carboxamide
61. N-[(1-(Pyrrolidin-1-yl) tricyclo[3.3.1.0$^{3,7}$]nonan-3-yl]-4-hydroxy-1-isopropyl-2-oxo-1,2-dihydroquinoline-3-carboxamide
62. N-[(1-(Pyrrolidin-1-yl) tricyclo[3.3.1.0$^{3,7}$]nonan-3-yl]-1-cyclopropyl-4-hydroxy-2-oxo-1,2-dihydroquinoline-3-carboxamide
63. N-[(1-(Pyrrolidin-1-yl) tricyclo[3.3.1.0$^{3,7}$]nonan-3-yl]-1-cyclohexyl-4-hydroxy-2-oxo-1,2-dihydroquinoline-3-carboxamide
64. N-(2-Methyl-2-azatricyclo[3.3.1.1$^{3,7}$]dec-5-ylmethyl)-4-hydroxy-1-isopropyl-2-oxo-1,2-dihydroquinoline-3-carboxamide
65. N-(2-Methyl-2-azatricyclo[3.3.1.1$^{3,7}$]dec-5-ylmethyl)-1-cyclopropyl-4-hydroxy-2-oxo-1,2-dihydroquinoline-3-carboxamide
66. N-(2-Methyl-2-azatricyclo[3.3.1.1$^{3,7}$]dec-5-ylmethyl)-1-benzyl-4-hydroxy-2-oxo-1,2-dihydroquinoline-3-carboxamide
67. N-(2-Methyl-2-azatricyclo[3.3.1.1$^{3,7}$]dec-5-ylmethyl)-4-hydroxy-1-isobutyl-2-oxo-1,2-dihydroquinoline-3-carboxamide
68. N-(2-Methyl-2-azatricyclo[3.3.1.1$^{3,7}$]dec-5-ylmethyl)-1-cyclohexyl-4-hydroxy-2-oxo-1,2-dihydroquinoline-3-carboxamide
69. N-(2-Ethyl-2-azatricyclo[3.3.1.1$^{3,7}$]dec-5-ylmethyl)-1-cyclopentyl-4-hydroxy-2-oxo-1,2-dihydroquinoline-3-carboxamide
70. N-[(5-Methoxy-2-azatricyclo[3.3.1.1$^{3,7}$]dec-2-yl)propyl]-4-hydroxy-1-isopropyl-2-oxo-1,2-dihydroquinoline-3-carboxamide
71. N-[(5-Butoxy-2-azatricyclo[3.3.1.1$^{3,7}$]dec-2-yl)propyl]-4-hydroxy-1-isopropyl-2-oxo-1,2-dihydroquinoline-3-carboxamide Biological Assays Example 72

Determination of $EC_{50}$ Values for 5-$HT_4$ Receptor

A stable CHO cell line expressing recombinant human 5-$HT_4$ receptor and pCRE-Luc reporter system was used for cell-based assay. The assay offers a non-radioactive based approach to determine binding of a compound to GPCRs. In this specific assay, the level of intracellular cyclic AMP which is modulated by activation or inhibition of the receptor is measured. The recombinant cells harbor luciferase reporter gene under the control of cAMP response element.

The above cells were grown in 96 well clear bottom white plates in Hams F12 medium containing 10% fetal bovine serum (FBS). Prior to the addition of compounds or standard agonist, cells were serum starved overnight. Increasing concentrations of test compounds were added in OptiMEM medium to the cells. The incubation was continued at 37° C. in $CO_2$ incubator for 4 hours. Medium was removed and cells were washed with phosphate buffered saline. The cells were lysed and luciferase activity was measured in a Luminometer. Luminescence units were plotted against the compound concentrations using Graphpad software. $EC_{50}$ values of the compounds were defined as the concentration required in stimulating the luciferase activity by 50%.

| Example Number | $EC_{50}$ (nM) |
|---|---|
| 1. | 230 |
| 2. | 4021 |
| 3. | 1109 |
| 4. | 421 |
| 5. | 1603 |
| 6. | 667 |
| 7. | 1000 |
| 8. | 3077 |
| 9. | 935 |
| 10. | 2799 |
| 11. | 3001 |
| 12. | 972 |
| 13. | 462 |
| 14. | 307 |
| 15. | 2728 |
| 16. | 3915 |
| 17. | 1146 |
| 18. | 958 |

-continued

| Example Number | $EC_{50}$ (nM) |
|---|---|
| 19. | 645 |
| 20. | 77 |
| 21. | 476 |

Literature References: Jeanne. M et al., Isolation of the serotoninergic 5-HT$_4$ receptor from human heart and comparative analysis of its pharmacological profile in C6-glial and CHO cell lines. Br. J. Pharmacol. 2001, 129, 771-781; Evgeni. G et al., 5-Hydroxytryptamine 4(a) Receptor is coupled to the $G_\alpha$ Subunit of Heterotrimeric $G_{13}$ Protein, J. Biol. Chem. 2002, 277(23), 20812-20819.

Example 73

Rodent Pharmacokinetic Study

Male Wister rats (230-280 grams) obtained from NIN (National Institute of Nutrition, Hyderabad, India) was used as an experimental animal. Three to five animals were housed in each cage. One day prior to dosing day, male wistar rats (225-250 grams) were anesthetized with isoflurane for surgical placement of jugular vein catheter. Animals were kept fasted over night and maintained on a 12 hours light/dark cycle. Three rats were dosed NCE (5 mg/Kg) orally and intravenously on day 0 and day 2.

At each time point blood was collected by jugular vein. Plasma was stored frozen at −20° C. until analysis. The concentrations of the NCE compound in plasma were determined using LC-MS/MS method. Schedule time points: Pre dose 0.25, 0.5, 1, 1.5, 2, 3, 4, 6, 8, 10, 12 and 24 hours after dosing (n=3). The NCE compounds were quantified in plasma by validated LC-MS/MS method using solid phase extraction technique. NCE compounds were quantified in the calibration range of 2-2000 ng/mL in plasma. Study samples were analyzed using calibration samples in the batch and quality control samples spread across the batch.

Pharmacokinetic parameters $C_{max}$, $T_{max}$, $AUC_t$, $T_{1/2}$ and Bioavailability were calculated by non-compartmental model using software WinNonlin version 5.0.1.

| Example Number | Strain/Gender | Dose (mg/kg) | Vehicle | Route of administration | $C_{max}$ (ng/mL) | $T_{max}$ (h) | $AUC_t$ (ng·hr/mL) | $T_{1/2}$ (h) | Bioavailability (%) |
|---|---|---|---|---|---|---|---|---|---|
| 1. | Wister/Male | 5 | Water | Oral | 211 ± 32 | 0.83 ± 0.29 | 801 ± 105 | 2.37 ± 0.60 | 26 ± 11 |
|  | Wister/Male | 5 | Water | Intravenous | 1167 ± 241 | 0.08 ± 0.00 | 3023 ± 980 | 1.88 ± 1.15 |  |
| 4. | Wister/Male | 5 | Water | Oral | 216 ± 78 | 0.33 0.14 | 547 ± 126 | 1.80 ± 0.36 | 34 ± 6 |
|  | Wister/Male | 5 | Water | Intravenous | 803 ± 62 | 0.08 0.00 | 1661 ± 498 | 2.64 ± 0.89 |  |
| 14. | Wister/Male | 5 | Water | Oral | 67 ± 17 | 0.42 ± 0.14 | 223 ± 50 | 1.67 ± 0.27 | 28 ± 3 |
|  | Wister/Male | 5 | Water | Intravenous | 523 ± 57 | 0.08 ± 0.00 | 820 ± 247 | 3.31 ± 1.47 |  |

Example 74

Rodent Brain Penetration Study

Male Wister rats (230-280 grams) obtained from NIN (National Institute of Nutrition, Hyderabad, India) was used as an experimental animal. Three animals were housed in each cage. Animals were given water and food ad libitum throughout the experiment, and maintained on a 12 hours light/dark cycle.

Brain penetration was determined in discrete manner in rats. One day prior to dosing day, male wistar rats (225-250 grams) were acclimatized. After acclimatization the rats were grouped according to the weight in each group, 3 animals were kept in individual cage and allowed free access to food and water. At each time point (0.5, 1, and 2 hours) n=3 animals were used.

NCE compound was dissolved in water and administered orally at (free base) 10 mg/kg. Blood samples were removed via, cardiac puncture by using isofurane anesthesia the animals were sacrificed to collect brain tissue. Plasma was separated and Brain samples were homogenized and stored frozen at −20° C. until analysis. The concentrations of the NCE compound in plasma and Brain were determined using LC-MS/MS method.

The NCE compounds were quantified in plasma and brain homogenate by validated LC-MS/MS method using solid phase extraction technique. NCE compounds were quantified in the calibration range of 1-500 ng/mL in plasma and brain homogenate. Study samples were analyzed using calibration samples in the batch and quality control samples spread across the batch. Extents of brain-blood ratio were calculated ($C_b/C_p$).

| Example Number | Strain/Gender | Dose (mg/kg) | Vehicle | Route of administration | Steady State Brain Penetration ($C_b/C_p$) |
|---|---|---|---|---|---|
| 1. | Wister/Male | 10 | Water | Oral | 0.20 ± 0.04 |
|  | Wister/Male | 10 | Water | Intravenous |  |
| 4. | Wister/Male | 10 | Water | Oral | 0.66 ± 0.10 |
|  | Wister/Male | 10 | Water | Intravenous |  |
| 14. | Wister/Male | 10 | Water | Oral | 2.97 ± 0.94 |
|  | Wister/Male | 10 | Water | Intravenous |  |

Example 75

Rodent Brain Micro Dialysis Study for Possible Modulation of Neurotransmitters

Male Sprague Dawley rats (230-280 grams) obtained from R.C.C. (RCC, Hyderabad, India) was used as experimental animals.

Group allocation Group 1: Vehicle (Water; 5 mL/kg; p.o.), Group 2: NCE (3 mg/kg; p.o.). Surgical Procedure: Rats were anesthetized with isoflurane and placed in Stereotaxic frame. Guide cannula (CMA/12) was placed in frontal cortex by using following coordinates AP: +3.2 mm, ML: −3.2 mm relative from bregma and DV: −1.0 mm from the brain surface according to the atlas of Paxinos and Watson (1986). While the animal was still anesthetized, a micro dialysis probe (CMA/12, 4 mm, PAES) was inserted through the guide cannula and secured in place. After surgery recovery period of 48-72 hours was maintained before subjecting the animal for study.

On the day of experiment, animals were transferred to home cages for acclimatization and implanted probe was perfused with a modified Ringer's solution comprised of: 1.3 µM CaCl2 (Sigma), 1.0 µM $MgCl_2$ (Sigma), 3.0 µM KCl (Sigma), 147.0 µM NaCl (Sigma), 1.0 µM $Na_2HPO_4.7H_2O$ and 0.2 µM $NaH_2PO_4.2H_2O$ (pH to 7.2) at a rate of 1.5 µL/minutes and allowed for 1 hours stabilization. After stabilization period, five basals were collected at 20 minutes intervals before dosing. Dialysate samples were collected in glass vials using CMA/170 refrigerated fraction collector.

Vehicle or NCE (3 mg/kg or 10 mg/kg) was administered by gavages after four fractions had been collected. The perfusate was collected until 4 hours after administration.

Acetylcholine concentrations in dialysate samples were measured by LC-MS/MS (API 4000, MDS SCIEX) method. Acetylcholine is quantified in the calibration range of 0.250 to 8.004 ng/mL in dialysates.

On completion of the microdialysis experiments, the animals were sacrificed and their brains were removed and stored in a 10% formalin solution. Each brain was sliced at 50µ on a cryostat (Leica) stained and examined microscopically to confirm probe placement. Data from animals with incorrect probe placement were discarded.

Microdialysis data were expressed as percent changes (Mean±S.E.M.) of baseline that was defined as the average absolute value (in fM/10 µL) of the four samples before drug administration.

Effects of NCE (3 mg/kg) and Vehicle treatments were statistically evaluated by one-way ANOVA followed by Dunnett's multiple comparison tests. In all statistical measures, a $p<0.05$ was considered significant. The Graph Pad Prism program statistically evaluated the data.

Example 76

Object Recognition Task Model

The cognition-enhancing properties of compounds of this invention were estimated using a model of animal cognition: the object recognition task model.

Male Wister rats (230-280 grams) obtained from N. I. N. (National Institute of Nutrition, Hyderabad, India) was used as experimental animals. Four animals were housed in each cage. Animals were kept on 20% food deprivation before one day and given water ad libitum throughout the experiment and maintained on a 12 hours light/dark cycle. Also the rats were habituated to individual arenas for 1 hour in the absence of any objects.

One group of 12 rats received vehicle (1 mL/Kg) orally and another set of animals received compound of the formula (I) either orally or i.p., before one hour of the familiar (T1) and choice trial (T2).

The experiment was carried out in a 50×50×50 cm open field made up of acrylic. In the familiarization phase (T1), the rats were placed individually in the open field for 3 minutes, in which two identical objects (plastic bottles, 12.5 cm height×5.5 cm diameter) covered in yellow masking tape alone (a1 and a2) were positioned in two adjacent corners, 10 cm. from the walls. After 24 hours of the (T1) trial for long-term memory test, the same rats were placed in the same arena as they were placed in (T1) trial. Choice phase (T2) rats were allowed to explore the open field for 3 minutes in presence of one familiar object (a3) and one novel object (b) (Amber color glass bottle, 12 cm high and 5 cm in diameter). Familiar objects presented similar textures, colors and sizes. During the T1 and T2 trial, explorations of each object (defined as sniffing, licking, chewing or having moving vibrissae whilst directing the nose towards the object at a distance of less than 1 cm) were recorded separately by stopwatch. Sitting on an object was not regarded as exploratory activity, however, it was rarely observed.

T1 is the total time spent exploring the familiar objects (a 1+a2).

T2 is the total time spent exploring the familiar object and novel object (a3+b).

The object recognition test was performed as described by Ennaceur, A., Delacour, J., 1988, A new one-trial test for neurobiological studies of memory in rats—Behavioural data, Behav. Brain Res., 31, 47-59.

Some representative compounds have shown positive effects indicating the increased novel object recognition viz; increased exploration time with novel object and higher discrimination index.

| Example Number | Dose mg/kg, p.o. | Exploration time mean ± S.E.M (sec) | | Inference |
|---|---|---|---|---|
| | | Familiar object | Novel object | |
| 1. | 10 mg/kg | 7.87 ± 0.83 | 12.56 ± 1.31 | Active |
| 4. | 10 mg/kg | 6.72 ± 1.92 | 11.86 ± 1.65 | Active |
| 19. | 1 mg/kg | 8.83 ± 1.54 | 14.09 ± 1.56 | Active |

Example 77

Water Maze

Water maze consisted of a 1.8 m diameter; 0.6 m high circular water maze tub filled with water. A platform was placed 1.0 cm below the water surface in the center of one of the four imaginary quadrants, which remained constant for all the rats. Rats were administered with vehicle or test compound before acquisition training and half hour after administration of vehicle or test compound; scopolamine was administered. Rats were lowered gently, feet first into water. A rat was allowed to swim for 60 seconds to find the platform. If the platform was found during this time the trial was stopped and rat was allowed to stay on platform for 30 seconds before being removed from the maze. If the platform was not found during 60 seconds trials, then the rat was manually placed on the platform. Each rat received 4 trials in a day. Retention of the task was assessed on 5th day in which each animal received a single 120 seconds probe trial in which platform removed from the pool. Time spent in target quadrant (ms) (quadrant in which platform is placed during acquisition training was calculated for probe trial. Latency to reach the platform (ms), swim speed (cm/s) and path length (cm) was measured in acquisition trials.

We claim:

1. A compound of the general formula (I),

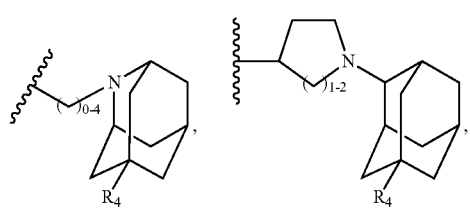

or a pharmaceutically acceptable salts thereof;
wherein,
$R_1$ represents hydrogen, hydroxy, halogen, nitro, amine, alkyl or alkoxy;
$R_2$ represents hydrogen, alkyl or aralkyl;
$R_3$ represents

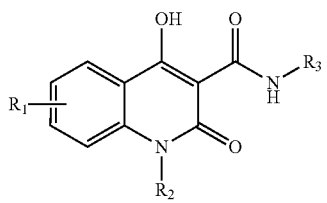

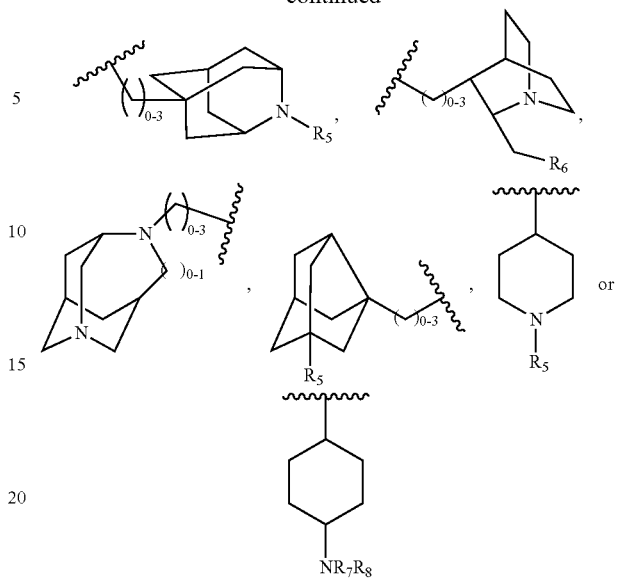

$R_4$ represents hydrogen, hydroxy, alkyl or aryl;
$R_5$ represents hydrogen, alkyl or heterocyclyl;
$R_6$ represents heteroaryl;
$R_7$ and $R_8$ along with 'N' atom form 5 to 7 member rings, which includes one or more heteroatoms selected from C, N, O or S.

2. The compound according to claim 1, which is selected from the group consisting of:
N-[(2-Azatricyclo[3.3.1.1$^{3,7}$]dec-2-yl)propyl]-4-hydroxy-1-isopropyl-2-oxo-1,2-dihydroquinoline-3-carboxamide hydrochloride;
N-[(2-Azatricyclo[3.3.1.1$^{3,7}$]dec-2-yl)propyl]-4-hydroxy-1-isobutyl-2-oxo-1,2-dihydroquinoline-3-carboxamide hydrochloride;
N-[1-(Tricyclo[3.3.1.1$^{3,7}$]dec-2-yl)pyrrolidin-3-yl]-4-hydroxy-1-isopropyl-2-oxo-1,2-dihydroquinoline-3-carboxamide;
N-[(5-Hydroxy-2-azatricyclo[3.3.1.1$^{3,7}$]dec-2-yl)propyl]-4-hydroxy-1-isopropyl-2-oxo-1,2-dihydroquinoline-3-carboxamide;
N-[(5-Phenyl-2-azatricyclo[3.3.1.1$^{3,7}$]dec-2-yl)propyl]-4-hydroxy-1-isopropyl-2-oxo-1,2-dihydroquinoline-3-carboxamide hydrochloride;
N-[(1,4-Diazatricyclo[4.3.1.1$^{3,8}$]undec-4-yl)propyl]-4-hydroxy-1-isopropyl-2-oxo-1,2-dihydro-quinoline-3-carboxamide;
N-[(2-Azatricyclo[3.3.1.1$^{3,7}$]dec-2-yl)propyl]-4-hydroxy-1-isobutyl-6-methoxy-2-oxo-1,2-dihydroquinoline-3-carboxamide;
N-[(2-Azatricyclo[3.3.1.1$^{3,7}$]dec-2-yl)propyl]-6-chloro-4-hydroxy-1-isopropyl-2-oxo-1,2-dihydroquinoline-3-carboxamide;
N-[(2-Azatricyclo[3.3.1.1$^{3,7}$]dec-2-yl)propyl]-6-fluoro-4-hydroxy-1-isopropyl-2-oxo-1,2-dihydroquinoline-3-carboxamide;
N-[(2-Azatricyclo[3.3.1.1$^{3,7}$]dec-2-yl)propyl]-6-bromo-4-hydroxy-1-isopropyl-2-oxo-1,2-dihydroquinoline-3-carboxamide;
N-[(2-Azatricyclo[3.3.1.1$^{3,7}$]dec-2-yl)propyl]-6-amino-4-hydroxy-1-isopropyl-2-oxo-1,2-dihydroquinoline-3-carboxamide;

N-[2-(Pyridin-3-ylmethyl)-1-azabicyclo[2.2.2]oct-3-yl]-4-hydroxy-1-isopropyl-2-oxo-1,2-dihydroquinoline-3-carboxamide;

N-[2-(Pyridin-2-ylmethyl)-1-azabicyclo[2.2.2]oct-3-yl]-4-hydroxy-1-isopropyl-2-oxo-1,2-dihydroquinoline-3-carboxamide;

N-(2-Methyl-2-azatricyclo[3.3.1.1$^{3,7}$]dec-5-yl)-4-hydroxy-1-isopropyl-2-oxo-1,2-dihydro-quinoline-3-carboxamide;

N-(2-Isopropyl-2-azatricyclo[3.3.1.1$^{3,7}$]dec-5-yl)-4-hydroxy-1-isopropyl-2-oxo-1,2-dihydro-quinoline-3-carboxamide;

N-(2-Benzyl-1-azabicyclo[2.2.2]oct-3-yl)-4-hydroxy-1-isopropyl-2-oxo-1,2-dihydroquinoline-3-carboxamide;

N-[(2-Azatricyclo[3.3.1.1$^{3,7}$]dec-2-yl)ethyl]-4-hydroxy-1-isopropyl-2-oxo-1,2-dihydroquinoline-3-carboxamide hydrochloride;

N-(2-Butyl-2-azatricyclo[3.3.1.1$^{3,7}$]dec-5-yl)-4-hydroxy-1-isopropyl-2-oxo-1,2-dihydroquinoline-3-carboxamide hydrochloride;

N-(2-Ethyl-2-azatricyclo[3.3.1.1$^{3,7}$]dec-5-ylmethyl)-4-hydroxy-1-isopropyl-2-oxo-1,2-dihydroquinoline-3-carboxamide hydrochloride;

N-(1-Butylpiperidin-4-yl)-4-hydroxy-1-isopropyl-2-oxo-1,2-dihydroquinoline-3-carboxamide hydrochloride;

N-[(1-(Pyrrolidin-1-yl)tricyclo[3.3.1.0$^{3,7}$]nonan-3-yl]-4-hydroxy-1-isopropyl-2-oxo-1,2-dihydro-quinoline-3-carboxamide;

N-[(2-Azatricyclo[3.3.1.1$^{3,7}$]dec-2-yl)propyl]-6-nitro-4-hydroxy-1-isopropyl-2-oxo-1,2-dihydroquinoline-3-carboxamide;

N-(2-Azatricyclo[3.3.1.1$^{3,7}$]dec-5-yl)-4-hydroxy-1-isopropyl-2-oxo-1,2-dihydroquinoline-3-carboxamide hydrochloride;

N-[(2-Azatricyclo[3.3.1.1$^{3,7}$]dec-2-yl)propyl]-4-hydroxy-1-methyl-2-oxo-1,2-dihydroquinoline-3-carboxamide hydrochloride;

N-[(2-Azatricyclo[3.3.1.1$^{3,7}$]dec-2-yl)propyl]-1-benzyl-4-hydroxy-2-oxo-1,2-dihydroquinoline-3-carboxamide hydrochloride;

N-[(4-(Morpholin-4-yl)cyclohexyl)-4-hydroxy-1-isopropyl-2-oxo-1,2-dihydroquinoline-3-carboxamide hydrochloride;

N-(4-(Pyrrolidin-1-yl)cyclohexyl)-4-hydroxy-1-isopropyl-2-oxo-1,2-dihydroquinoline-3-carboxamide hydrochloride; or their pharmaceutically acceptable salts.

3. A process for the preparation of a compound of formula (I) as claimed in claim 1, which comprises:

reacting of ester compound of formula (59)

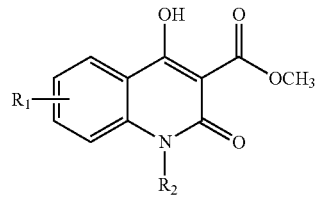

(59)

with amine compound

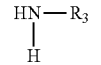

amine compound using suitable solvent to obtain a compound of formula (I), wherein all substitutions as defined in claim 1.

4. A pharmaceutical composition comprising a compound according claims 1 and pharmaceutically acceptable excipient, wherein said composition is for treating Alzheimer's disease or pain.

5. A method for modulating the 5-HT$_4$ receptor, in a patient in need thereof, which comprises providing to said patient a therapeutically effective amount of a compound of formula (I) as defined in claim 1.

6. A method for treating a disorder selected from Alzheimer's disease or pain, in a patient in need thereof, which comprises providing to said patient a therapeutically effective amount of a compound of formula (I) as defined in claim 1.

* * * * *